(12) United States Patent
Geboers et al.

(10) Patent No.: US 9,150,486 B2
(45) Date of Patent: Oct. 6, 2015

(54) METHOD FOR THE PRODUCTION OF CONJUGATED POLYUNSATURATED FATTY ACIDS WITH HETEROGENOUS CATALYSTS

(75) Inventors: Jan Geboers, Zonhoven (BE); Steven Goossens, Heverlee (BE); An Philippaerts, Hasselt (BE); Bert Sels, Balen (BE)

(73) Assignee: Katholieke Universiteit Leuven, Leuven (BE)

(*) Notice: Subject to any disclaimer, the term of this patent is extended or adjusted under 35 U.S.C. 154(b) by 9 days.

(21) Appl. No.: 13/989,608

(22) PCT Filed: Nov. 24, 2011

(86) PCT No.: PCT/BE2011/000067
§ 371 (c)(1),
(2), (4) Date: May 24, 2013

(87) PCT Pub. No.: WO2012/068645
PCT Pub. Date: May 31, 2012

(65) Prior Publication Data
US 2013/0245299 A1    Sep. 19, 2013

(30) Foreign Application Priority Data

Nov. 25, 2010  (GB) .................................. 1019961.0
Feb. 21, 2011  (GB) .................................. 1102962.6
Mar. 21, 2011  (GB) .................................. 1104698.4

(51) Int. Cl.
*C11C 3/00*  (2006.01)
*C01B 33/36*  (2006.01)
(Continued)

(52) U.S. Cl.
CPC .............. *C07C 51/353* (2013.01); *B01J 29/10* (2013.01); *B01J 29/126* (2013.01); *B01J 29/20* (2013.01); *B01J 29/42* (2013.01); *B01J 29/44* (2013.01); *B01J 29/7215* (2013.01); *B01J 29/74* (2013.01); *B01J 29/7415* (2013.01); *C11C 3/14* (2013.01); *B01J 2229/16* (2013.01); *B01J 2229/36* (2013.01); *B01J 2229/38* (2013.01)

(58) Field of Classification Search
CPC ...... C01B 39/02; C01B 39/026; B01J 20/186; B01J 29/70; B01J 29/084; B01J 2229/16; B01J 2229/36; C10G 11/05; C11C 3/14; C07C 51/353; C07C 67/333; C07C 51/09; C07C 51/42
USPC .................................. 554/126; 423/700, 713
See application file for complete search history.

(56) References Cited

U.S. PATENT DOCUMENTS 4,456,693 A    6/1984 Welsh

OTHER PUBLICATIONS

Bernas, et al.: "Isomerization of linoleic acid over supported metal catalysts", Applied Catalysis A: General., vol. 245, 2003, pp. 257-275.*

(Continued)

*Primary Examiner* — Deborah D Carr
(74) *Attorney, Agent, or Firm* — Fitch, Even, Tabin & Flannery LLP

(57) ABSTRACT

The present invention relates to an improved process for the production of conjugated polyunsaturated fatty acids (PUFA), preferably conjugated linoleic acid (CLA), using finely dispersed heterogeneous metal catalysts on a mesoporous support, in the absence of Hg. The present invention also relates to a method to increase the large microporosity and (optionally) the small mesoporosity of a zeolite, thus obtaining a modified zeolite having a large and highly accessible internal surface.

17 Claims, 9 Drawing Sheets

(51) Int. Cl.
| | |
|---|---|
| *C01B 39/00* | (2006.01) |
| *C01B 7/00* | (2006.01) |
| *C07C 51/353* | (2006.01) |
| *C11C 3/14* | (2006.01) |
| *B01J 29/10* | (2006.01) |
| *B01J 29/12* | (2006.01) |
| *B01J 29/20* | (2006.01) |
| *B01J 29/42* | (2006.01) |
| *B01J 29/72* | (2006.01) |
| *B01J 29/44* | (2006.01) |
| *B01J 29/74* | (2006.01) |

(56) References Cited

OTHER PUBLICATIONS

Martens, et al., "Forty Years of Designing Catalytic and Adsorptive Sites in FAU Type Zeolites at K.U. Leuven." Topics in Catalysis, vol. 52, Apr. 28, 2009, pp. 1119-1130.

Zou, et al., "Pretreatment Chemistry in the Preparation of Silica-Supported Pt, Ru, and Pt-Ru Catalysts: An in Situ UV Diffuse Reflectance Study." Journal of Catalysis vol. 133, (1992), pp. 202-219.

Simakova, et al., "Linoleic acid isomerization over mesoporous carbon supported gold catalysts." Catalysis Today vol. 150, Aug. 7, 2009, pp. 32-36.

Bauer, et al., "Direct Isomerization of Linoleic Acid to Conjugated Linoleic Acids (CLA) using Gold Catalysts." Chemical Engineering & Technology 2009 vol. 32 No. 12, pp. 2005-2010.

Bernas, et al., "Influence of ruthenium precursor on catalytic activity of Ru/Al2O3 catalyst in selective isomerization of linoleic acid to cis-9, trans-11- and trans-10, cis-12-conjugated linoleic acid." Applied Catalysis A: General vol. 267, Apr. 12, 2004, pp. 121-133.

Chorfa, et al., "Conjugated linoleic acid formation via heterogeneous hydrogenation/isomerization of safflower oil over mesostructured catalysts." Applied Catalysis A: General vol. 387, Aug. 11, 2010, pp. 75-86.

Jung, et al., "Effects of Temperature and Agitation Reate on the Formation of Conjugated Linoleic Acids in Soybean Oil during Hydrogenation Process." Journal of Agricultural and Food Chemistry vol. 49, No. 6, May 17, 2001, pp. 3010-3016.

Jung, et al., "CLA Formation in Oils During Hydrogenation Process as Affected by Catalyst Types, Catalyst Contents, Hydrogen Pressure, and Oil Species." Journal of the American Oil Chemists' Society vol. 79, No. 5, 2002, pp. 501-510.

Pertici, et al., "(n6-Naphthalene)(n4-cycloocta-1,5-diene)ruthenium(0) as efficient catalytic precursor for the isomerization of methyl linoleate under mild conditions." Journal of Molecular Catalysis A: Chemical vol. 144, (1999), pp. 7-13.

International Application No. PCT/BE2011/000067, International Search Report, Jun. 1, 2012, 4 pages.

International Application No. PCT/BE2011/000067, International Preliminary Report on Patentability, Dec. 5, 2012, 12 pages.

International Application No. PCT/BE2011/000067, Written Opinion of the International Searching Authority, Jun. 1, 2012, 4 pages.

* cited by examiner

METHOD FOR THE PRODUCTION OF CONJUGATED POLYUNSATURATED FATTY ACIDS WITH HETEROGENOUS CATALYSTS

CROSS REFERENCE TO RELATED APPLICATIONS

This application is a national phase application of International Application No. PCT/BE2011/000067, filed Nov. 24, 2011, designating the United States and claiming priority to British Patent Application No. 1019961.0, filed Nov. 25, 2010, British Patent Application No. 1102962.6, filed Feb. 21, 2011, and British Patent Application No. 1104698.4, filed Mar. 21, 2011, all of which are incorporated by reference as if fully rewritten herein.

FIELD OF THE INVENTION

The present invention relates to an improved process for the production of conjugated polyunsaturated fatty acids (PUFA) using heterogeneous metal catalysts on an inorganic nanoporous support. The present invention also relates to said improved heterogeneous catalyst having a modified intracrystalline structure with an increased large micropore volume allowing the metal to be highly dispersed, and to the use of said catalyst for the conversion of PUFAs to conjugated PUFAs.

BACKGROUND OF THE INVENTION

Two types of naturally occurring polyunsaturated fatty acids (PUFA) can be distinguished, based on the relative position of double bonds: i.e. (i) fatty acids with isolated double bonds, such as linoleic acid (C18:2), and (ii) fatty acids having conjugated double bonds. Linoleic acid is a major component in vegetable oils, with soybean and safflower oil typically containing linoleic acid levels up to 53.7% and 77.7%, respectively. Fatty acids with conjugated double bonds occur relatively rarely in natural fats. However, conjugated fatty acids have gained increasing importance in recent years because of their nutritional and technological properties.

From a technological point of view, conjugated fatty acids find use as drying oils in paints, varnishes and plastics. Drying oils polymerize or "dry" after they have been applied to a surface to form tough, adherent and abrasion resistant films. As conjugated double bonds are more reactive than unconjugated ones, CLAs are also used as co-monomers in the production of bio-plastics via cationic and free radical copolymerization. Tung oil is an example of a naturally occurring oil containing significant levels of conjugated fatty acids. Because tung oil is expensive for many industrial applications, research was conducted in order to find substitutes.

In the particular case of conjugated linoleic acid (CLA), i.e. the positional and geometric conjugated dienoic isomers of linoleic acid (C18:2, which can have either the cis or trans configuration), the cis-9,trans-11 isomer of CLA (c9,t11-CLA, rumenic acid) is by far the predominant form in foods (as much as 90% of the total CLA content), especially in milk and tissue fat of ruminants. Synthetic CLA mixtures consist mostly of c9,t11- and t10,c12-CLA in almost equal amounts, with traces of t9,t11- and t10,t12-CLAs.

A variety of positive health effects have been attributed to CLAs. They are claimed to be anticarcinogenic, antidiabetic, antioxidative and antiarteriosclerotic. They decrease fat and increase muscle content in the body, reduce inflammation, show a beneficial effect on bone formation, enhance immune functions and reduce asthma (Bhattacharya et al, 2006). Recent studies conducted with enriched preparations in either c9,t11- or either t10,c12-CLA show that the two isomers assess different biological activity. Several reviews summarize the health effects of CLA mixtures and the purified form of c9,t11- and t10c12-CLA isomers (Bhattacharya et al., 2006; Pariza et al., 2001). Next to the c9,t11- and the t10,c12-CLA isomer, the t9,t11-CLA also exhibit beneficial health effects, which are superior compared with the more abundant c9,t11- and t10,c12-CLAs (Coakley et al., 2006; Ecker et al., 2009; Lee & Vanden Heuvel, 2010).

Because of their technological and nutritional applications, several isomerisation reactions to convert fatty acids having isolated double bonds into fatty acids having conjugated double bonds have been developed.

Conjugated PUFA Production Via Alkaline Isomerisation

In the alkali isomerization process, PUFA, such as linoleic acid, or an oil rich in PUFA or linoleic acid, like safflower oil, is treated at high temperature (200-250° C.) under alkaline conditions and an inert atmosphere ($N_2$). In the current commercial processes strong bases, like NaOH or KOH, dissolved in water, are used. During the alkaline treatment isomerization as well as saponification takes place. As a consequence, the triglyceride structure is broken and glycerol and soaps are formed. Afterwards the aqueous phase, containing glycerol and the homogeneous base, is separated and the soaps are treated with an acid (mostly citric acid) in order to convert them to free fatty acids. In this process mainly the c9,t11 and the t10,c12-CLA isomers are formed in almost equal amounts.

Some improvements of the commercial alkaline isomerisation include, for example, the use of organic solvents with a high boiling point, like ethylene glycol and propylene glycol, instead of water. This way, the reaction can be conducted under the boiling point of the solvent (at 130-150° C. compared to 200-250° C. in the aqueous process), which leads to a better temperature and pressure control, and shorter reaction times (2.5-6 hours). Moreover, the selectivity to the c9,t11- and the t10,c12-CLA isomer is higher (Saebo et al, 2002).

Homogeneous, basic catalysts can also be used for the production of conjugated CLA esters. In this process, alkali metal alcoholate catalysts are used, which in contrast to KOH and NaOH, do not hydrolyze the ester bond. The use of high amounts of bases is often a problem in the industrial process because this lead to corrosion of the reactor.

In the context of the alkaline isomerisation, esterification of conjugated PUFAs/CLAs or either transesterification of conjugated PUFA/CLA alkyl esters is required to obtain triacylglycerols (TAGs) containing conjugated PUFA/CLA.

Conjugated PUFA Production Using Homogeneous Metal Complexes

Different homogeneous catalysts have been tested for the preparation of conjugated fatty acids and oils:

Cr-complexes, such as arene-$Cr(CO)_3$ complexes and $Cr(CO)_6$ (Frankel, 1970), Rh-complexes, for example $RhCl_3$, $[(C_6H_5)_3P]_3RhCl$ (DeJarlais and Gast, 1971ab; Singer et al, 1972, 1977), $[(C_6H_5)_3P]_2RhCOCl$ (Singer et al, 1972) and $[RhCl (C_8H_{14})_2]_2$ (Larock et al, 2001), Pt-complexes, as cis-$Cl_2[(C_6H_5)_3P]_2PtSnCl_2$ and $PtCl_2(PPh_3)_2$ (DeJarlais and Gast, 1971, Larock et al, 2001), and Ru-complexes, such as $Ru(\eta^6\text{-naphthalene})(\eta^4\text{-cycloocta-1,5-diene})$ (Pertici et al., 1999) and $RuHCl(CO)(PPh_3)_3$ (Larock et al., 2001).

The substrates can be fatty acids like linoleate as well as polyunsaturated oils, for example soybean or safflower oils.

Like the isomerization reaction in strong alkali, several conjugated products are formed. These systems are characterised by low reaction temperatures, high selectivity towards CLA, and the fact that TAGs enriched in CLA can be produced directly. However, the main drawback of these systems is that the catalysts are soluble homogeneous metal complexes, which are not environmentally friendly and difficult to separate from the reaction medium or products. The reuse of such catalysts and the ligands and the use of high amounts of solvents are often problematic. In the particular case when the conjugated PUFA/CLA product will be used in food applications, the choice of the solvent will be limited and also only very low metal contamination levels are acceptable.

Conjugated PUFA Production Via Heterogeneous Catalysis

Heterogeneous catalysis (i.e. a metal catalyst deposited on a porous anorganic or carbon support with a large internal surface) constitutes an attractive strategy for sustainable CLA production, as the catalyst can be separated and reused easily. Although some heterogeneous processes for isomerisation of linoleic acid or methyl linoleate have already been described in literature, low productivity is the main drawback.

Different metals and supports have been screened for the production of CLA, including:
- a Ru/C catalyst in the isomerization of methyllinoleate (Mukesh et al, 1985; Narasimhan et al, 1985; Deshpande et al, 1985)
- a Rh/C catalyst for the isomerization of methyllinoleate (Deshpande et al, 1985)
- Ru on different supports ($\gamma$-$Al_2O_3$, $SiO_2Al_2O_3$, C and MgO) and in combination with Ni (Mukesh et al, 1988).

However, besides isomerization also hydrogenation (formation of oleate, elaïdate and stearate), polymerization and coke formation was observed.

Bernas et al (2003) and Bernas et al (2004) screened Ru, Ni, Pd, Pt, Rh, Ir, Os, and bimetallic Pt—Rh supported by activated carbon, $Al_2O_3$, $SiO_2Al_2O_3$, MCM-22, H-MCM-41, H-Y and H-BETA for the isomerization reaction of linoleic acid to CLA. In order to enhance the isomerization reaction a two-step process was used. In a pre-activation step the catalyst surface is first saturated with hydrogen and then the isomerization reaction of linoleic acid to CLA occurs under a $N_2$ atmosphere. However, significant quantities of hydrogenated products, such as oleic acid, were formed.

Kreich and Claus (2005) described a highly selective method for the synthesis of CLAs over heterogeneous silver catalysts and in the constant presence of hydrogen. Also, the use of heterogeneous gold catalysts were tested in the isomerization of linoleic acid under constant hydrogen flow. Depending on the Au catalyst used, isomerization or hydrogenation is favored (Bauer et al, 2009; Simakova et al., 2010).

One of the main disadvantages of the heterogeneous catalyst based isomerization processes is that the productivities in the heterogeneous processes are very low compared to the industrial process using homogeneous bases. Another difficulty in the heterogeneous catalyzed process is the competition between isomerization and hydrogenation. While isomerization can take place in both directions (i.e. from conjugated to isolated double bonds and vice versa), hydrogenation is a consecutive reaction which only goes in one direction and lowers the CLA yield. On the one hand, hydrogen is needed in order to form the half-hydrogenated intermediates which leads to the isomerization of linoleic acid to CLAs, on the other hand too high levels of hydrogen will lead to the formation of unwanted hydrogenated products. Hence, the direct production of CLA using heterogeneous catalysts is a difficult and complicated process.

In this respect, partially hydrogenated vegetable oils contain higher levels of CLAs, indicating that during the hydrogenation of vegetable oils (using heterogeneous catalysts) CLAs are formed (Mossoba et al., 1991; Banni et al., 1994). By finetuning the hydrogenation process increasing levels of CLAs can be accumulated. The isomerization/hydrogenation ratio can be influenced by the catalyst used as well as the reaction conditions. High CLA accumulation requires conducting the hydrogenation at a high temperature, a low hydrogen pressure, a low agitation rate and a high catalyst level (Jung et al., 2001, 2002). However, these conditions also favor the formation of the unwanted C18:1 trans-isomers, which are known to increase the risk of cardiovascular diseases.

Finally, Chorfa et al (2010) described the hydrogenation/isomerization of safflower oil using a rhodium loaded mesoporous molecular sieve. The reaction was conducted at 180° C. and low hydrogen pressure (0.3 bar). The main isomers formed are the c9,t11-, t10,c12- and t,t-CLAs.

In short, the production of conjugated polyunsaturated fatty acids and derivatives thereof, known in the art, has several disadvantages:
- In the alkaline conversion of nonconjugated PUFA, the alkali bases, solvents and acids used are disadvantageous from an ecological and economic point of view. Also an extra processing step is needed to neutralise and/or remove the alkaline catalyst. Furthermore, a mixture of different conjugated PUFA isomers is obtained instead of a single PUFA isomer. Also, the use of conjugated PUFA, such as CLA, in food application requires conjugated PUFA enriched TAGs (and not as free fatty acids or FAMEs), which cannot be obtained directly by the use of homogeneous bases due to the saponification. Thus, an extra time-consuming esterification or transesterification of conjugated PUFA (CLA) (as fatty acid or methylester derivative thereof) is needed.
- The main drawback of using homogeneous metal complexes is that these catalysts are soluble in the reaction medium, which makes them difficult to separate and is not environmentally friendly. In addition, when the conjugated PUFA or CLA product will be used in food applications, the choice of the solvent will be limited and very low metal contamination levels are required (from food safety point of view and to minimize the oxidation of the unsaturated fatty acids).
- The main disadvantage in the heterogeneous production of conjugated PUFA or derivatives thereof, particularly in the presence of $H_2$ or similar compounds, is the competition between hydrogenation and isomerization. Although changing the process conditions can aid in minimizing the hydrogenation reaction and hence the formation of hydrogenated byproducts, the reaction conditions which have a positive influence on the isomerization reaction also favor the production of harmful C18:1 trans-isomers.

There hence remains a need for novel methods to produce conjugated polyunsaturated fatty acids and derivatives thereof, such as the alkylesters thereof (e.g. PUFA methylester) or glycerides, particularly triglycerides, comprising said conjugated PUFA.

Accordingly, the present invention provides a new heterogeneous isomerisation catalyst for the synthesis of conjugated PUFA in the absence of hydrogen, as well as novel methods for the synthesis of conjugated PUFA using said heterogeneous catalyst, particularly in the absence of hydrogen.

SUMMARY OF THE INVENTION

A first object of the present invention provides a method for preparing conjugated polyunsaturated fatty acids (PUFAs) by isomerisation of a nonconjugated PUFA comprising contacting a starting material containing a nonconjugated PUFA with a heterogeneous catalyst containing a finely dispersed metal loaded on an inorganic nanoporous Si based support with a large internal surface and wherein the dispersion of said metal as calculated by CO chemosorption is at least 30%, preferably at least 40%, 50%, 60% or 70%, most preferably at least 80% or 90%. Preferably, said isomerisation method according to the present invention occurs in the absence of $H_2$ in the reaction medium or associated with the catalyst, such as following preactivation of the catalyst by $H_2$.

In a preferred embodiment of the isomerisation method according to the present invention said finely dispersed metal is a noble metal or Ni, more preferably said finely dispersed metal is Ru or Rh.

In another preferred embodiment said inorganic nanoporous Si based support is a mesoporous zeolite or zeolite-like material having microporous and mesoporous porosity, predominantly having large micropores and (optionally) small mesopores. Preferably, said inorganic nanoporous Si based support has a Si/Al ratio of at least 30, more preferably has a Si/Al ratio of at least 40. Preferably, the Brønsted acidity of the heterogeneous catalyst is reduced or low by using large monovalent cations, preferably large monovalent alkali metal cations, such as $Na^+$, $K^+$, $Rb^+$ and $Cs^+$, to balance the negative charge of the framework of the support. In a particular embodiment of the isomerisation method according to the present invention said heterogeneous catalyst is a Ru/Cs or Rh/Cs loaded zeolite of the MFI-, BEA-, MOR- or FAU-type.

In yet another preferred embodiment of the isomerisation method according to the present invention said PUFA in said starting material containing nonconjugated PUFA, is a free fatty acid or is esterified with an alcohol or glycerol. Preferably, said PUFA is linoleic acid or linolenic acid. Preferably, said starting material containing nonconjugated PUFA is an oil or fat.

In another preferred embodiment the isomerisation reaction according to the present invention is carried out in an inert or oxygen free atmosphere. In yet another preferred embodiment the isomerisation reaction according to the present invention is carried out in solvent free conditions.

A second object of the present invention relates to a method for modifying a zeolite or zeolite-like material to increase the large microporosity, while the large mesoporosity is unaffected, and/or to increase the metal dispersion of a catalytic metal loaded zeolite or zeolite-like material. Said method for the modification of a zeolite, particularly the modification of the pore architecture of said zeolite, comprises the step of treating said zeolite with a $NH_4OH$-solution, preferably a $NH_4OH$-solution with a concentration below 0.05 M, more preferably ranging from 0.001 to 0.03 M. In a preferred embodiment said method for the modification of a zeolite further comprises the step of introducing a catalytic metal in said zeolite. Any process known in the art suitable for introducing a catalytic metal in a zeolite may be used in the context of the present invention. In yet another preferred embodiment, said zeolite is first (partially) dealuminated by steaming or acid leaching to introduce mesoporosity in said zeolite.

Another object of the present invention provides a zeolite obtainable by the above method for modification of the zeolite pore architecture. Preferably, said modified zeolite has a framework of the type FAU, MFI, BEA, FER or MOR. In a particular embodiment, said modified zeolite is a FAU-type zeolite with a mesopore volume ranging between 0.10 and 0.30 mL/g, a micropore volume of at least 0.2 mL/g and a large micropore volume of at least 0.15 mL/g.

Said modified zeolite according to the present invention are particularly useful as catalysts of acylation, alkylation, dimerization, oligomerization, polymerization, hydrogenation, dehydrogenation, aromatization, isomerisation, hydrotreating, catalytic cracking and hydrocracking reactions. Particularly, a modified zeolite according to the present invention loaded with a finely dispersed noble metal or Ni, preferably Ru or Rh, is particularly useful as a catalyst of PUFA isomerisation reactions, in particular in oils and fats.

DETAILED DESCRIPTION

Legends to the Figures

Figure 7A:
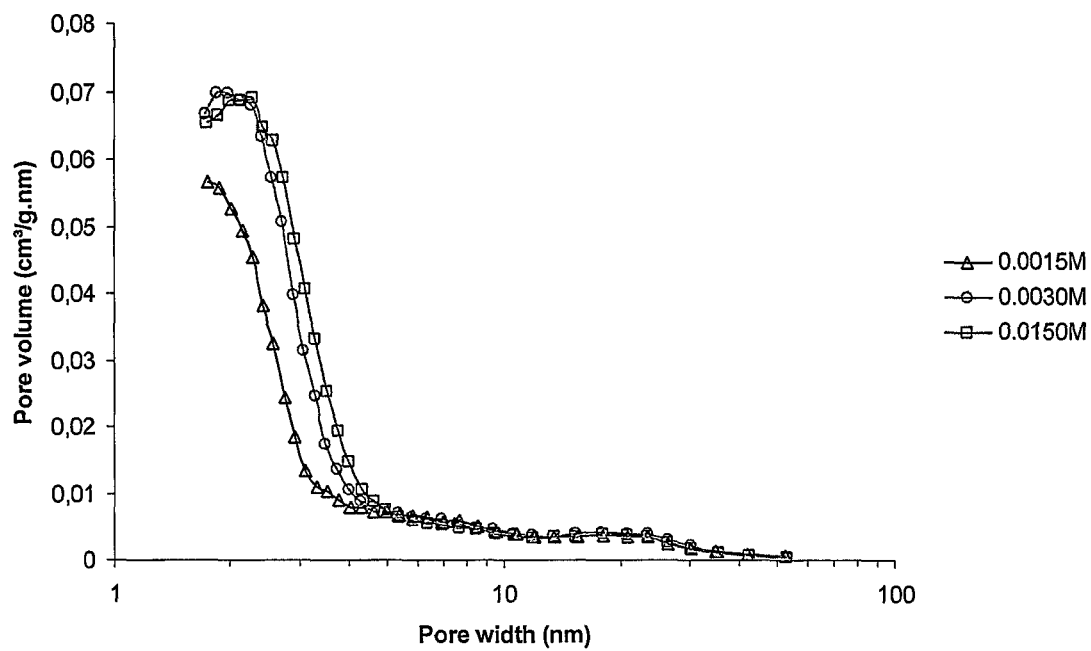
FIG. 7A shows the BJH mesopore size distribution of the $NH_4OH$-treated USY samples.
Figure 7B:
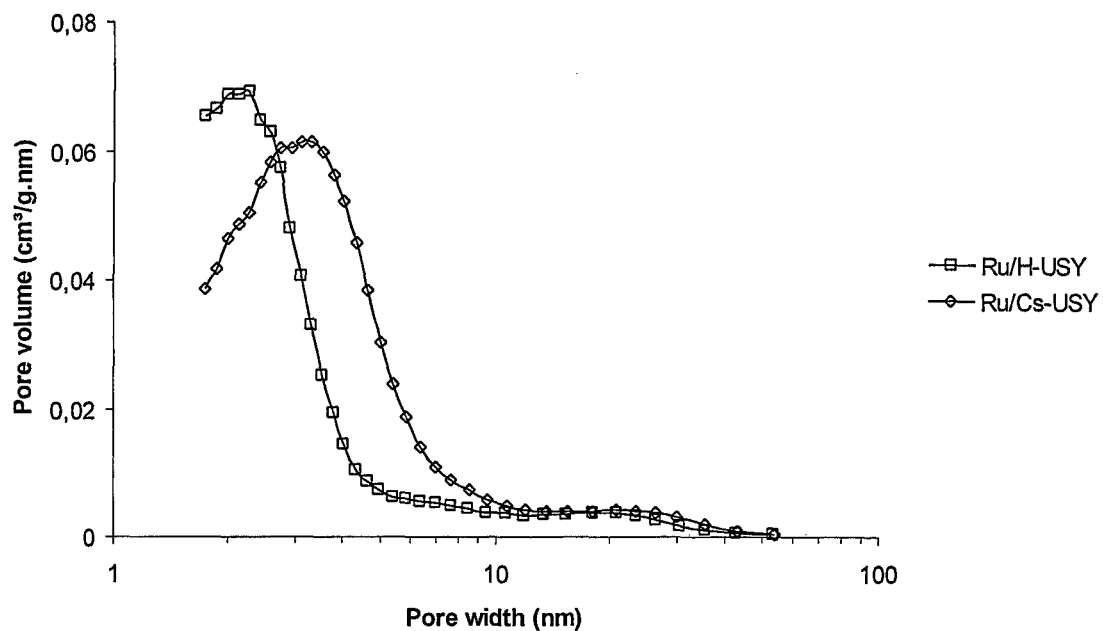
Figure 8:
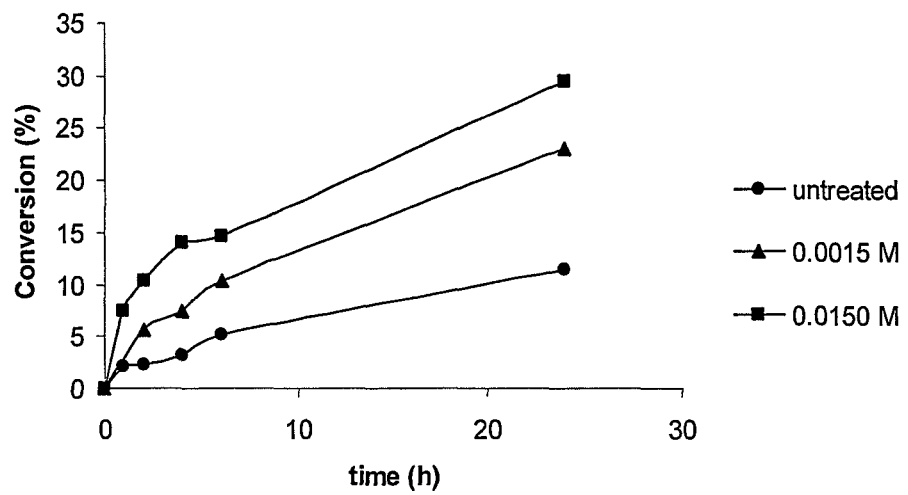

FIG. 7B shows the BJH mesopore size distribution plot of the Ru/H-USY and the Ru/Cs-USY catalyst, treated with 0.0150 M $NH_4OH$ FIG. 8 shows the conversion of linoleate in the isomerisation of safflower oil in absence of solvent at 180° C. under $N_2$ atmosphere using different 0.5 wt % Ru/H-USY catalysts, prepared by treating the parent USY support (CBV780) with different $NH_4OH$ concentrations.

Figure 9:
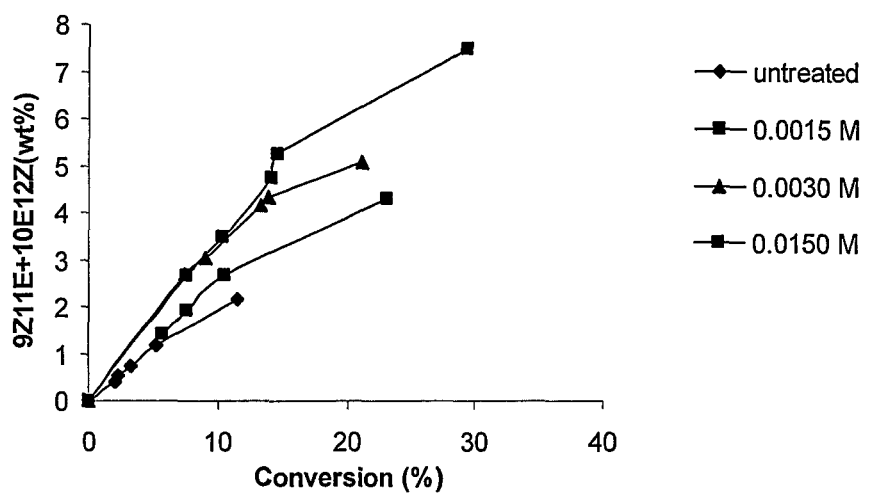

FIG. 9 shows the yield of desirable cis-9,trans-11- and trans-10,cis-12-CLA in function of conversion for different 0.5 wt % Ru/H-USY catalysts, prepared by treating the parent USY support (CBV780) with different $NH_4OH$ concentrations. Reaction conditions: isomerisation of safflower oil in absence of solvent at 180° C. under $N_2$ atmosphere.

Figure 10:
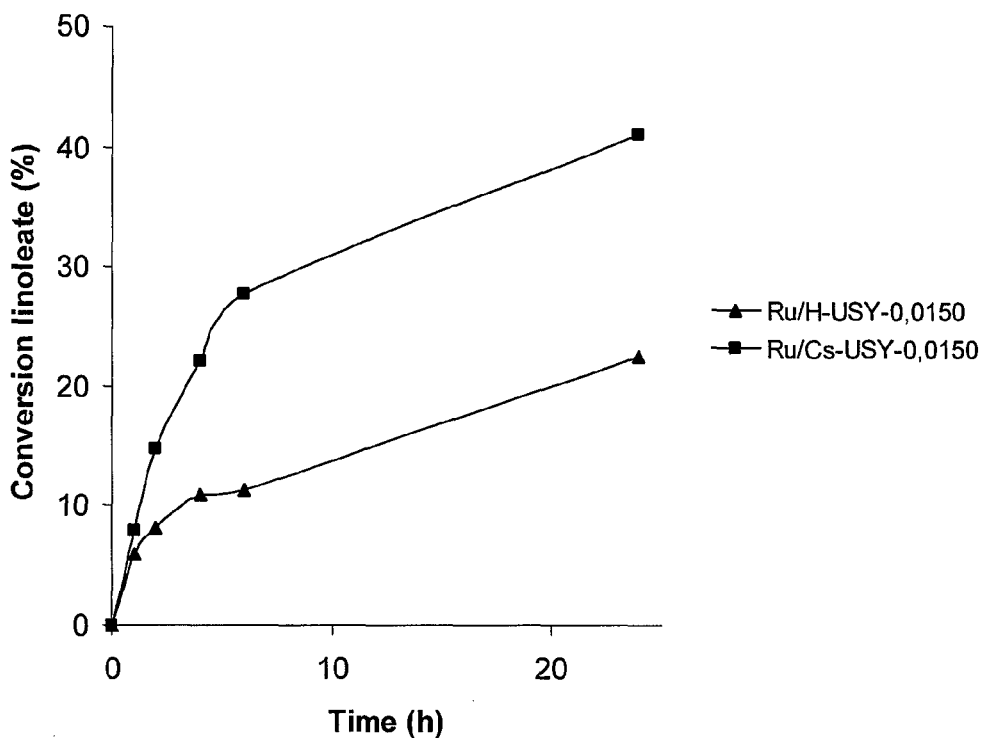

FIG. 10 compares the conversion of linoleate in the isomerisation of safflower oil in absence of solvent at 180° C. under $N_2$ atmosphere using a 0.5 wt % Ru/H-USY and a 0.5 wt % Ru/Cs-USY catalyst, prepared by treating the parent USY support (CBV780) with 0.0150M $NH_4OH$.

Figure 11:
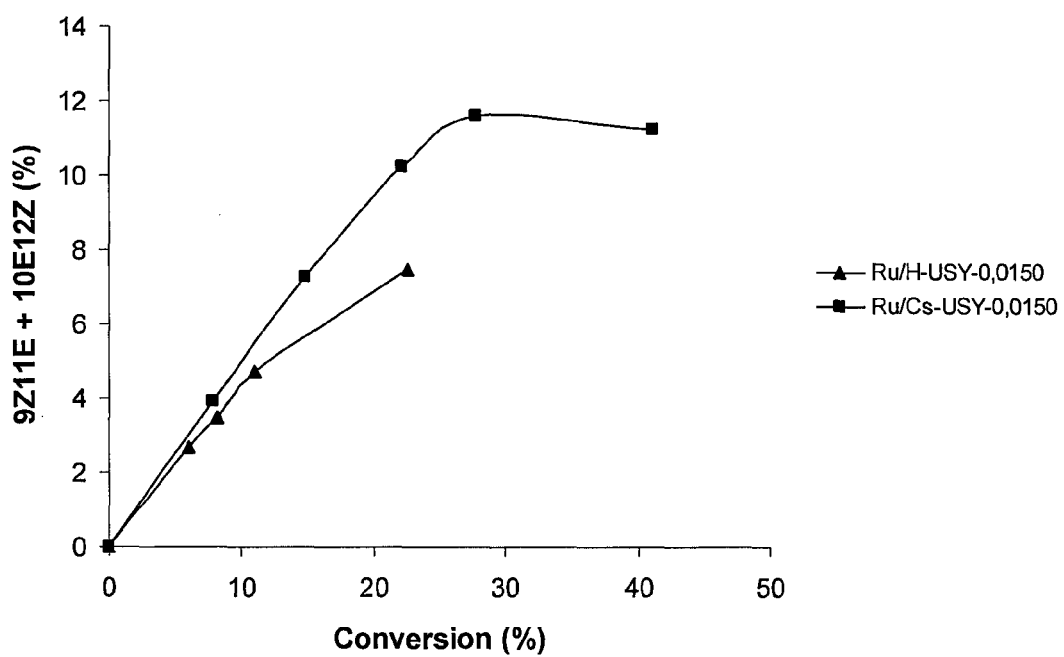

FIG. 11 shows the yield of desirable cis-9,trans-11- and trans-10,cis-12-CLA in function of conversion for a 0.5 wt % Ru/H-USY and a 0.5 Ru/Cs-USY catalyst, prepared by treating the parent USY support (CBV780) with 0.0150 M NH$_4$OH. Reaction conditions: isomerisation of safflower oil in absence of solvent at 180° C. under N$_2$ atmosphere.

DETAILED DESCRIPTION

During the study of the isomerisation of a polyunsaturated fatty acid (linoleic acid) to its conjugated form (CLA), the inventors developed a process to selectively produce conjugated PUFAs in high yields based on a newly developed improved heterogeneous catalyst, comprising a metal (Ru) supported on an inorganic nanoporous Si based (zeolite) support. Particularly, said metal (Ru) is very finely dispersed in said support. Preferably, said zeolite support in itself may be first treated to increase the large microporosity and the metal dispersion prior to preparation and metal (Ru) loading of said zeolite, while at the same time the large mesoporosity of said zeolite is largely unaffected, thus creating a nanoporous support with large internal surface and easily accessible to PUFA containing glycerides, including triglycerides. Preferably, the charge compensating cations in said inorganic nanoporous Si based support are the larger monovalent alkali metal cations to reduce the Brønsted acidity of said support. Advantageously, said novel conjugated PUFA production process occurs without a source of H$_2$ or without preactivating the heterogeneous catalyst with H$_2$. Advantageously, very low levels of hydrogenation products (in particular the unwanted transC18:1) are formed. Advantageously, in the case of the isomerisation of linoleic acid, the c9,t11-, t10,c12- and t9,t11-CLA isomers are selectively formed. Advantageously, vegetable oils, rich in PUFAs such as linoleic acid, can be treated by said process without addition of solvents in a one-step reaction and without a source of H$_2$ to obtain vegetable oils enriched in conjugated PUFAs (e.g. CLA), particularly enriched in c9,t11-, t10,c12- and t9,t11-CLA.

DEFINITIONS

A "fatty acid" is preferably an unbranched carboxylic acid, preferably having an even number of carbon atoms (n). In the context of the present invention, preferred fatty acids have from n=6 to n=24 carbon atoms, more preferably from n=8 to n=22, even more preferably from n=12 to n=22 carbon atoms, particularly preferably from n=16 to n=22 carbon atoms, such as 18 carbon atoms.

In the context of the present invention, the (polyunsaturated) fatty acid can be present in/as a saponifiable or non-saponifiable molecule. The saponifiable fatty acid compounds comprise esters, mono-, di and triglycerides, phospholipids, glycolipids, diol esters of fatty acids, waxes and sterol esters. The non-saponifiable compounds comprise free fatty acids, sterols, carotenoids, monoterpenes and tocopherols. Preferably, the fatty acid, or polyunsaturated fatty acid can be present as a free fatty acid, or salt thereof, as an esterified fatty acid, as/in a glyceride or triglyceride, and/or in an oil or fat.

A "polyunsaturated fatty acid" or PUFA is a fatty acid having at least two double bonds, which can be conjugated or non-conjugated. If not specified otherwise, "polyunsaturated fatty acid" generally refers to fatty acids containing non-conjugated double bonds. A "conjugated polyunsaturated fatty acid" is an unsaturated fatty acid having at least two double bonds that are conjugated. The non-conjugated, polyunsaturated fatty acid has two double bonds which are at positions n and n+3, for example in the case of linoleic acid or linolenic acid, where n is a carbon of the carboxylic acid or fatty acid. Preferred PUFA can be isomerized to form conjugated PUFA, for example to form conjugated linoleic acid (CLA), α-parinaric acid (18:4 octadecatetraenoic acid), eleostearic acid (18:3 octadecatrienoic acid), dimorphecolic acid, conjugated linolenic acids and calendic acid, with particular preference given to CLA preparations which comprise c9,t11-CLA, t10,c12-CLA and/or t9,t11-CLA isomers as reaction products.

An "esterified polyunsaturated fatty acid" refers to PUFA esterified with an alcohol or glycerol. Preferred alcohols are C$_1$- to C$_5$-alcohols, for example methanol, ethanol, propanol, isopropanol, n-butanol, isobutanol tert-butanol, or n-pentanol and its isomers (2-pentanol, 3-pentanol, 2-hydroxy-3-methylbutane). Particular preference is given to methanol and ethanol. Said alcohol can be bound to other carbons or heteroatoms, for example H, O, S, P, halogens. Preferably, the esterified PUFA is present as a glyceride, or triglyceride.

"Inorganic nanoporous materials". In the context of the present invention, inorganic nanoporous materials support the catalytic metal species. Preferred inorganic nanoporous materials include zeolites and zeolite-like materials, ordered mesoporous materials and hierarchical materials presenting more than one level of porosity and structural order. More particularly the term "zeolite" refers to zeolites and zeolite-like material having a zeolite framework of the type AEI, AEL, AFI, AFO, AFR, AFX, ATN, ATO, BEA, CDO, CFI, CHA, CON, DDR, DON, EMT, EON, EUO, FAU, FER, IFR, IHW, ISV, ITE, ITH, ITW, IWR, IWV, IWW, LEV, LTA, LTL, MAZ, MEI, MEL, MER, MFI, MFS, MOR, MOZ, MSE, MSO, MTF, MTN, MTT, MTW, MWW, NON, RRO, RTE, RTH, RWR, SFE, SFF, SFG, SFH, SFN, SGT, SSY, STF, STT, TON or TUN (http://izasc.ethz.ch/fmi/xsl/IZA-SC/ft.xsl). Ordered microporous and mesoporous materials can be described in terms of a host structure, which defines a pore structure, which may have a free volume contain guest species (such as charge-compensating cations). The voids between the linked atoms have a free volume larger than a sphere with a 0.25 nm diameter. Pores with free diameters of less than 2 nm are called "micropores", and those in the range of 2 to 50 nm "mesopores". In the context of the present invention "small micropores" have a diameter of less than 1.5 nm, while "large micropores" have a diameter in the range of 1.5 to 2 nm. In the context of the present invention, the mesopores includes both small mesopores (between 2 and 5 nm) and large mesopores (>10 nm). Pore volumes and pore diameters can be estimated by nitrogen physisorption. For example, micropore volumes can be determined by the t-plot method as described in Gregg, S. J., Sing, K. S. W., Adsorption, Surface and Porosity, Academic Press, 1982, p. 94+209, while mesopore size distribution can be determined by the BJH-method as described in Rouquerol et al., Adsorption by powders and porous solids, Academic Press, San Diego, 1999, p. 199.

When the atoms of the host as well as the voids are arranged periodically with long-range order (at least 10 repeats in all directions) the zeolites or zeolite-like materials produce sharp maxima in a diffraction experiment. These materials are crystalline. Chemically, zeolites are mixed oxides. In general, zeolites and zeolite-like materials are (crystalline) aluminosilicates in which the three components aluminium, silicon and oxygen are arranged in a fixed, 3-dimensional framework. Other, secundary elements, including titanium, gallium, boron, iron and cobalt, may be incorporated in the framework. This framework structure may contain linked cages, cavities or channels, which are of the right size to allow small molecules to enter. The zeolite network is typically composed of SiO$_4$ and AlO$_4$ tetrahedra in which the negative charge on the framework is neutralised by the positive charges of cations in non-framework positions, like metal ions, protons, ammonium ions or alkali metal ions. Next to crystalline microporous materials and ordered mesoporous materials both having only one type of pores, poly-porous materials exist. A distinction can be made according to the ordering of the different types of porosity. Mesoporous zeolites have a secondary porosity composed of irregular mesopores in addition to the micropores. Methods for mesopore formation in zeolites, known in the art, include dealumination by steaming or acid leaching or desilication in alkaline medium. For instance, the ultrastable Y zeolite as a result of dealumination and partial structure degradation (by steaming) presents intracrystalline mesopores in addition to micropores.

Isomerisation of PUFA to Conjugated PUFA

A first object of the invention relates to a method for preparing a conjugated polyunsaturated fatty acid (or stated differently, a method for the isomerisation of PUFAs), whereby said method comprises contacting a nonconjugated polyunsaturated fatty acid containing start material with a heterogeneous catalyst comprising a metal supported on a nanoporous inorganic Si based support with a large internal surface. In a preferred embodiment, said catalytic metal is highly dispersed on said support. In another preferred embodiment said process for preparing conjugated polyunsaturated fatty acids occurs in the absence of $H_2$ in the reaction medium or associated with the catalyst. In the absence of $H_2$ is in the meaning that no $H_2$ is used in the preparation of the catalyst, such as to preactivate the heterogeneous catalyst, nor is the isomerisation reaction performed in the presence of hydrogen gas (either pure or as a mixture with an inert gas).

Said nanoporous inorganic Si based support is preferably a zeolite or zeolite-like material, more preferably a mesoporous zeolite or zeolite-like material, having a secondary mesoporous porosity in addition to its microporosity. Such mesoporosity includes both small mesopores (between 2 and 5 nm) as large mesopores (>10 nm). Large mesopores may be obtained by e.g. steaming. Preferably, said support is further modified to increase the dispersion of the catalytic metal by increasing the large microporosity and (optionally) the small mesoporisity of said zeolite or zeolite-like material. Examples of said treatment include the method discussed below in the section "zeolite modification" (e.g. a 0.015M aqueous $NH_4OH$ solution) or contacting the support with a (strong) alkaline solution (e.g. a KOH or NaOH solution as described in WO2010072976). Preferably, said nanoporous inorganic Si based support is rich in Si and has a Si/Al ratio of at least 30, more preferably at least 40.

Said catalytic metal is preferably a metal capable of catalysing hydrogenation reactions, such as noble metals (Ru, Pd, Pt, Au, Ag, Rh, Ir and Os), or Ni. Most preferably, said metal is Ru or Rh. In the context of the present invention, said metal is finely dispersed on said nanoporous inorganic Si based support. Typically, the metal dispersion, which is related to the size of the metal cluster, is calculated from the CO chemisorption data of the heterogeneous catalyst, and assuming the adsorption of 1 CO per accessible metal atom. CO chemisorption of the heterogeneous catalyst can be determined by titration of the metal containing catalyst with pulses of pure CO and continuously quantifying the CO concentration in the outlet stream (e.g. by mass spectrometry—m/e (CO)=28). Preferably, a finely dispersed metal catalyst refers to a metal dispersion of at least 30%, 40% or 50%, more preferably at least 60% or 70%, most preferably at least 75% or 80%. Preferably, pore architecture of the support and the metal dispersion is improved by treating the nanoporous inorganic Si based support with an alkaline solution, such as an aqueous $NH_4OH$ solution, preferably a diluted aqueous $NH_4OH$ solution, prior to loading the metal catalyst on the support. Surprisingly, the inventors found that such $NH_4OH$-treatment created more large micropores and (optionally, depending on the $NH_4OH$ treatment conditions) more small mesopores, with pore size ranging between 1.5 and 4 nm, preferably between 1.5 and 2 or 3 nm, while at the same time the large mesoporosity was largely unaffected. This way, a zeolite support can be created with an enhanced internal surface and highly accessible pore structure (accessible to both free fatty acids and esterified fatty acids, including those present in triglycerides and oils/fats), and metal dispersion is enhanced upon loading the catalytic metal on the support.

Thus, preferred heterogeneous catalysts for the isomerisation of PUFA according to the present invention comprise a highly dispersed catalytic metal on a mesoporous zeolite support, wherein said mesoporous zeolite has a large internal surface. A large internal surface means that said zeolite contains a highly accessible pore architecture with both meso- and micropores, preferably large and small mesopores and large micropores. Preferred catalysts include Ru- or Rh-loaded MFI-type zeolites (such as ZSM-5), BEA-type zeolites (such as BETA), FAU-type zeolites (such as USY) or MOR-type zeolites, preferably having a Si/Al ratio of at least 30, more preferably at least 40. Preferably, the Brønsted acidity of said mesoporous zeolite is reduced, preferably substantially reduced or even absent, such as by the use of or presence of larger charge-compensating monovalent cations (which are used to balance the negative charge of the zeolite framework), preferably a larger alkali metal cation such as $Cs^+$, $Rb^+$, $K^+$ and/or $Na^+$, thus increasing the selectivity for conjugated PUFA. Preferably, the Brønsted acidity is lower than 0.04 mmol/g, most preferably lower than 0.02 or 0.01 mmol/g, as measured by pyridine-IR adsorption at 250° C. Particularly preferred heterogeneous catalysts are Ru-USY or Rh-USY catalysts, such as Ru/Cs-USY, Ru/Rb-USY, Ru/K-USY, Ru/Na-USY, Ru/Li-USY or Ru/H-USY or Rh/Cs-USY, Rh/Rb-USY, Rh/K-USY, Rh/Na-USY, Rh/Li-USY or Rh/H-USY or, more preferably Rh/Cs-USY and Ru/Cs-USY.

In a particular embodiment of the present invention the metal content of said inorganic nanoporous material supported metal catalyst ranges from 0.1 to 5.0 wt %, more preferably from 0.1 to about 2.0 wt % or from about 0.2 to about 1.0 wt %, most preferably from about 0.25 to 0.75 wt %, such as 0.4 to 0.7 wt %.

In another preferred embodiment of the present invention the ratio metal to non-conjugated PUFA in the reaction medium is below 5 or 4 wt %, more preferably below 3, below 2 or below 1.5 wt %, even more preferably below 1 or 0.5 wt %, most preferably below 0.2 or 0.1 wt %, such as between 0.03 and 0.005 wt %.

Advantageously, the heterogeneous catalyst can be used in solvent-free conditions. Alternatively, suitable solvents as known by the person skilled in the art, including but not limited to organic solvents, such as alcohols (e.g. octanol) or alkanes (e.g n-decane), can be used as reaction media. Furthermore, the heterogeneous catalysts can be separated from the reaction medium by means of simple centrifugation, filtration, decantation, or by other liquid-solid separation techniques thus allowing recycling of the catalyst.

Typically, the isomerisation reaction according to the present invention is performed at temperatures between 120° C. and 220° C., more preferably between 140° C. and 200° C. or between 140° C. and 180° C. The reaction may be carried out at pressures between 1.0 and 5.0 bar. Preferably, during the reaction, an inert atmosphere is maintained above the reaction mixture. Suitable oxygen-free atmosphere can be created by using gases like nitrogen, helium, argon and/or carbon dioxide or by applying a vacuum.

In yet another preferred embodiment the unconjugated PUFA containing starting material comprises linoleic acid which after isomerization according to the present invention is converted in CLA, preferably selectively converted in c9,t11-CLA, t10,c12-CLA or t9,t11-CLA. Thus the present invention provides a method for selectively preparing c9,t11-CLA, t10,c12-CLA or t9,t11-CLA from linoleic acid by contacting a linoleic acid containing feed, such as an oil, with a heterogeneous noble metal (Ru or Rh) loaded zeolite having a large internal surface, wherein said noble metal (Ru or Rh) is finely dispersed, and preferably in the absence of $H_2$ in the reaction medium or associated with the catalyst.

In yet another preferred embodiment of the present invention said PUFA in said PUFA containing starting material is an esterified PUFA, such as a PUFA methyl ester or a PUFA containing glyceride. More preferably, said PUFA containing feed is a PUFA containing triglyceride, or an oil or fat.

In this context, it has surprisingly been found that by means of the isomerization process according to the present invention, PUFA, for example linoleic acid, present in a glyceride, such as a triglyceride, such as in oil or fat, can be converted to the conjugated PUFA (e.g. CLA) contained in the (tri)glyceride, without prior release of the fatty acids, thus eliminating the need for an esterification or a transesterification reaction.

Thus, another preferred embodiment of the present invention relates to a process for preparing conjugated PUFA containing glycerides comprising contacting a nonconjugated polyunsaturated fatty acid present in a glyceride or glyceride mixture, such as an oil or fat, with a heterogeneous, finely dispersed catalytic metal supported on a nanoporous inorganic Si based support with a large internal surface. Preferably, a finely dispersed metal catalyst refers to a metal dispersion on said support of at least 40% or 50%, more preferably at least 60% or 70%, most preferably at least 75% or 80%, as determined by CO chemisorption. Preferably, said process occurs in the absence of $H_2$ in the reaction medium or associated with the catalyst. In a preferred embodiment the metal/lipid content in the reaction medium is below 1 wt %, more preferably below 0.05 wt %, such as between 0.03 and 0.005 wt %.

In the context of the present invention, a "glyceride" is glycerol or a derivative thereof esterified with one, two or three carboxylic acid radicals (mono-, di- or triglyceride). Said glyceride can also be present in a synthetic or naturally occurring glyceride oil or a derivative or mixtures thereof. "Glyceride" can also be taken to mean, depending on the context, synthetic or naturally occurring fatty acid esters and/or oils and fats comprising glycerides, also referred to as "glyceride mixture" below. A glyceride can be present in a mixture of different glycerides ("glyceride mixture"), which can comprise other additives, for example free fatty acids, antioxidants, proteins, carbohydrates, vitamins and other substances. In addition to the above described glycerides of fatty acids, glycerides of derivatives derived from glycerol, such as glycerophospholipids and glyceroglycolipids, are also contemplated. Preference is given here to the glycerophospholipids such as lecithin (phosphatidylcholine), cardiolipin, phosphatidylglycerol, phosphatidylserine and alkylacylglycerophospholipids, such as plasmalogen. In particular, derivatives in which the fatty acid composition of the naturally-occurring non-conjugated or saturated glycerides has not substantially changed are included.

In the context of the present invention, preferred PUFA containing starting materials are glycerides or mixtures of glycerides, in particular of mono-, di- or triglycerides, that are esterified with at least one, preferably two or three, polyunsaturated fatty acids. Therefore, preferred PUFA containing starting material includes synthetic or natural glycerides or glyceride mixtures which contain fatty acids having from n=6 to n=24 carbon atoms, more preferably from n=12 to n=22 carbon atoms or from n=16 to n=22 carbon atoms, particularly having 18 carbon atoms. Particularly, natural oils and fats which contain PUFA having more than 16 carbons and less than 22 carbons, preferably from 18 to 20 carbons are preferred.

The term "oil" or "fat" is taken to mean a mixture of fatty acids that comprises unsaturated, non-conjugated, esterified fatty-acid(s), in particular linoleic acid. Preferably, the oil or fat has a high content of unsaturated, non-conjugated esterified fatty acid(s), in particular linoleic acid. Preferably, the content of non-conjugated esterified PUFA is approximately 30%, more preferably is about 50%, still more preferably is about 60%, 70%, 80%, 90% or more. Fatty acid content determination is well known in the art and can, for example, be performed by gas chromatography after converting the fatty acids into the methyl esters by transesterification. The oil or fat can comprise various other saturated or unsaturated fatty acids, for example, palmitic acid, stearic acid, oleic acid, etc. In particular, depending on the preparation method, the content of the various fatty acids in the oil or fat can vary.

Each fatty acid profile is included by the inventive preparation, in particular fatty acid profiles which are produced in the production of oil from vegetable material. Preferably, the fatty acid esters are present as a glyceride, in particular as a triglyceride. In the context of the present invention, the glyceride mixture is preferably of animal, microbial or vegetable origin, for example olive oil, canola oil, coconut oil, coconut fat, sesame seed oil, rice germ oil, bamboo oil, bamboo fat, sunflower seed oil, rapeseed oil, fish oil, tallow oil, soybean oil, palm oil, safflower oil, linseed oil, wheat germ oil, peanut oil, cottonseed oil, corn oil, pig fat, beef fat, poultry fat, milk fat, tung oil or shea oil or a derivative or a mixture thereof. Particular preference is given in particular to oils and fats which have a high content of linoleic acid, for example sunflower seed oil, soybean oil, cottonseed oil, corn oil or wheat germ oil, safflower oil, thistle oil, rapeseed oil and in particular oils or fats from modified plant cultivars, in particular what are termed high linoleic seeds, for example linola (from linseed oil).

The PUFA containing starting material can also be produced by conventional processes known to those skilled in the art, for example oil from plants. Oil can be produced by pressing, for example, seed having a high husk content, or husked seed. For pressing and production, in addition to vegetable seed, other plants parts, for example leaves, tubers, stems, blossoms, fruits etc. of suitable plants can also be used which have a high content of unsaturated fatty acids, preferably esterified in triglycerides. Whole plants can also be used. The pressed material can also be pressed repeatedly. Other materials which are also suitable for producing oils and fats suitable for the inventive process are microorganisms, such as *Thraustochytrium* or *Schizochytrium* strains, algae such as *Phaeodactylum tricornutum* or *Crypthecodinium* species, ciliates, such as *Stylonychia* or *Colpidium*, fungi such as *Mortierella*, e.g. *Mortierella alpina, Entomorphthora* or *Mucor*. By means of strain selection, a number of mutant strains of the corresponding microorganisms have been developed that produce a series of desirable compounds, including PUFAs and which are also suitable for producing said fatty acids or oils. In particular microorganisms can be produced by suitable transformations, for example using nucleic acid molecules coding for desaturases or elongases.

Another specific advantage of this invention is that the obtained conjugated PUFA, whether esterified or not, are substantially free from by-products, such as hydrogenated fatty acids, in particular the transC18:1 fatty acid. Thus, another object of the present invention relates to a conjugated PUFA composition obtainable by the methods according to the present invention. In a preferred embodiment the conjugated PUFA composition comprise free conjugated PUFAs, or esterified conjugated PUFAs, such as glycerides containing conjugated PUFAs or a mixture of such glycerides, wherein the ratio tC18:1/PUFA, in particular tC18:1/CLA is very low, such as below 2%, more preferably below 1%.

Modification of the Zeolite Pore Architecture and Zeolites Having a Modified Pore Architecture Another object of the present invention relates to a method for the modification of a zeolite or zeolite-like material, particular for the modification of its pore structure, in order to increase the large microporosity of said zeolite or zeolite-like material, while at the same time its large mesoporosity is unaffected, and/or in order to increase the metal dispersion of a metal catalyst supported by said zeolite or zeolite-like material. In the context of the present invention "increased or enhanced large microporosity" refers to an increased volume of pores having a pore size of 1.5-2 nm, as determined by the t-plot method. In particular, the large micropore volume is relatively higher compared to that of the unmodified zeolite or zeolite-like material. Optionally, the small mesoporosity may be increased as well. However, it is understood that the present method for modification of a zeolite has only a limited, preferably no impact on the large mesoporosity, i.e. on the volume of pores ranging from 10 to 40 nm. This way, a modified zeolite with a large internal surface, which is highly accessible to a wide range of guest molecules, can be obtained, wherein, after loading of said modified zeolite with a catalytic metal, said catalytic metal is finely dispersed on said zeolite and able to efficiently act on said guest molecules.

Thus, the present invention provides a method for the modification of a zeolite or zeolite-like material comprising the step of (i) treating said zeolite or zeolite-like material with a weak $NH_4OH$-solution, preferably an $NH_4OH$-solution having a concentration lower than 0.05 M, more preferably an $NH_4OH$-solution having a concentration below 0.03 M, such as ranging between 0.001 M and 0.02 M. Typically, the $NH_4OH$ treatment occurs at atmospheric pressure at temperatures ranging from 0 to 60° C., such as from 10 to 40° C., preferably at room temperature, Preferably, said method further comprises the step of (ii) introducing a metal catalyst in the treated zeolite or zeolite-like material by methods known to the person skilled in the art (e.g. via ion-exchange or impregnation). Said catalytic metal is preferably a noble metal (Ru, Pd, Pt, Au, Ag, Rh, Ir and Os), Ni, Cu, Co, W, Mb or another transition metal.

The modified zeolites or zeolite-like materials can be recovered by filtration or centrifugation and may be further activated at elevated temperatures by methods know to the person skilled in the art, including calcination in air or oxygen gas at temperatures ranging from 400 to 700° C., using nitrogen gas at temperatures ranging from 200 to 500° C., or reduction by $H_2$.

Preferably, said zeolite or zeolite-like material to be modified is a mesoporous zeolite having a secondary porosity composed of mesopores (such as irregular mesopores) in addition to the micropores. Thus, the method for modifying a zeolite may comprise a first step of (0) introducing mesopores in said zeolite or zeolite-like material. Methods for mesopore formation in zeolites, known in the art, include dealumination by steaming or acid leaching or desilication in alkaline medium.

Preferred zeolites or zeolite-like materials to be modified by the present invention include MFI-type zeolites (such as ZSM-5), BEA-type zeolites (such as BETA), FAU-type zeolites (such as Y or USY), FER or MOR-type zeolites. Preferably, said zeolites have been (partially) dealuminated by steaming or acid leaching. Preferably, said zeolites have a Si/Al ratio between 1 and 250, more preferably between 20 and 250, such as between 30 or 40 and 200.

The present invention further relates to a zeolite or zeolite-like material, modified by the above described method for the modification of a zeolite or zeolite-like material. Said modified zeolite has an increased microporosity (1.5 to 2 nm) and (optionally) an increased small mesoporosity (2 to 5 nm, particularly between 2 and 4 nm) compared to the starting (unmodified) zeolite material, while the large mesoporosity is substantially similar to that of the unmodified zeolite material. Preferably, said modified zeolite acts as a support for a heterogeneous finely dispersed metal catalyst. A finely dispersed metal catalyst refers to a metal dispersion of at least 30%, 40% or 50%, more preferably at least 60% or 70%, most preferably at least 75% or 80%, as determined by CO adsorption. Said catalytic metal is preferably a noble metal (Ru, Pd, Pt, Au, Ag, Rh, Ir and Os), Ni, Cu, Co, W, Mb, or another transition metal.

Preferably, said modified zeolite or zeolite-like materials include modified (optionally partially dealuminated) MFI-type zeolites (such as ZSM-5), BEA-type zeolites (such as BETA), FAU-type zeolites (such as Y or USY), FER- or MOR-type zeolites.

In a particular embodiment said modified zeolite is a modified Fau-type zeolite, preferably an Y or USY zeolite, having a mesopore volume ranging between 0.10 and 0.30 mL/g, preferably ranging between 0.12 and 0.25 ml/g, more preferably ranging between 0.15 and 0.20 mL/g. It is understood that the large mesopore volume of the modified zeolite is highly similar to that of the unmodified zeolite; and a micropore volume of at least 0.2 mL/g, preferably ranging between 0.20 and 0.40 mL/g, more preferably ranging between 0.20 and 0.32 mL/g, whereby the large micropore volume is at least 0.15 mL/g.

Said modified Fau-type zeolite, preferably an Y or USY zeolite, is further characterised by a ratio of the total mesopore volume to the total micropore volume lower than 1, preferably ranging between 0.5 and 1.

Another aspect of the present invention relates to catalytic particles comprising a modified zeolite according to the present invention. Said modified zeolite may further comprise a catalytic metal.

Said modified zeolite according to the present invention or said catalytic particle comprising a modified zeolite according to the present invention may be used as catalysts for acylation, alkylation, dimerization, oligomerization, polymerization, hydrogenation, dehydrogenation, aromatization, isomerisation, hydrotreating, catalytic cracking and hydrocracking reactions, as known by the person skilled in the art. The large and highly accessible internal surface and/or the high dispersion of the catalytic metal is beneficial for the catalytic properties of the modified zeolite.

In a particular embodiment of the present invention, said modified zeolite or zeolite-like material according to the present invention acting as the support for a finely dispersed noble metal or Ni, preferably Ru or Rh, is ideally suited for catalysing the isomerisation reaction of unconjugated PUFAs to their conjugated counterparts. Said PUFA may be present as free fatty acids or esterified to an alcohol or glycerol. Preferably, said modified zeolite or zeolite-like material according to the present invention acting as the support for a finely dispersed noble metal or Ni, preferably Ru or Rh, catalyses the isomerisation reaction of unconjugated PUFAs in an oil or fat to their conjugated counterparts, without need for saponification, esterification or transesterification reactions.

The following examples are presented in order to more fully illustrate the preferred embodiments of the invention. They should in no way be construed, however, as limiting the broad scope of the invention.

EXPERIMENTAL

Material.

Zeolite samples used as support were from Zeolyst (ZSM-5=CBV28014, Y=CBV100, USY=CBV720, CBV760 and CBV780, BETA=CP811C-300), whereas the commercial Ru/C catalyst was from Johnson Matthey (5 wt % Ru, Type 97).

Catalyst Preparation.

The supports were loaded with 0.5 wt % of Ruthenium by ion exchange for 24 h under stirring of the aqueous zeolite slurry, containing the required amount of Ru, precursor (Ru (III)$(NH_3)_6Cl_3$) in a 200 mL water per gram of dry zeolite. Afterwards, the Ru-hexamine exchanged zeolite powder was filtered, washed with distilled water and dried overnight at 50° C. Prior to metal loading, the zeolite powder was changed from the proton to the $NH_4$-form by slurrying in an ammonia aqueous solution (0.015 M) for 16 h (200 mL/g). The obtained $NH_4$-zeolite was transformed in the Na-form via two successive room temperature ion-exchange steps (16 h) with 200 mL of an aqueous 1 M NaCl solution per g of dry zeolite. The Cs-form was obtained by exchanging the Na-zeolite twice with a 0.1 M aqueous Cs-acetate solution (25 mL/g zeolite) for 48 and 72 h, respectively. After each exchange step, the slurry is filtered, the solids washed three times with distilled water and air dried at 100° C.

Prior to activation the dry powders are compressed, crushed and sieved. The 0.25-0.50 mm fraction was retained for further use. Activation was conducted in a flow reactor in two steps under flowing nitrogen (120 mL/min/g). First the reactor was heated from room temperature to 200° C. at 2° C./min and then from 200 to 350° C. at 3° C./min. Optionally, a reduction step at 400° C. (5° C./min) under flowing hydrogen (120 mL/min/g) was performed.

Catalyst Characterization.

Nitrogen Physisorption.

Zeolite materials were first pretreated under $N_2$ at 250° C. for 12 hours in a SmartPrep degassing system (Micromeritics), in order to remove residual water. Physisorption measurements were performed on a TriStar (Micromeritics) gas adsorption analysis instrument.

Ruthenium dispersions were determined using CO-chemisorption. Catalyst pellets loaded in a tubular reactor were activated according to the pre-treatment procedure described previously and cooled down to room temperature under flowing helium. For the titration of the Ru surface, pulses of 5 μL of pure CO at an interval of 2 min were added to a helium flow of 10 mL/min. The CO concentration in the outlet stream was followed continuously via ion monitoring at m/e=28 with a Pfeiffer Omnistar quadrupole mass spectrometer. For the calculation of the dispersion, adsorption of 1 CO per accessible Ru atom was assumed. In the same way pulses of pure $H_2$ or pure $O_2$ were added to a helium flow for the $H_2$ and $O_2$ titration experiments, respectively. The concentration of $H_2$ and $O_2$ in the outlet stream was determined via ion monitoring at m/e=2 and 32, respectively. The same set-up was also used for the determination of the decomposition products during the activation of the catalysts under $N_2$. By monitoring at m/e=16, 17 and 18, the concentrations of $NH_2^+$, $NH_3$ and $H_2O$ species were followed, respectively.

Thermo-gravimetrical analysis (TGA) was performed on a TGA Q500 (TA Instruments) while heating the sample from room temperature till 700° C. (5° C./min) under oxygen.

Isomerisation Reaction.

Isomerization of methyl linoleate (ML) at 165° C. was carried out in a 100 mL Parr-autoclave with sampling device and under 3.5 bar of $N_2$ under constant stirring (500 rpm). In a typical experiment, 40 g n-decane, 0.1-5.0 g methyl linoleate and 0.8 g 0.5Ru-zeolite catalyst (or 5Ru/C) were used. Catalysts were pretreated in nitrogen at 350° C.

Fame Analysis.

The fatty acid methyl esters were analyzed using a Hewlett Packard HP 6890 gas chromatograph with a split injection system (split ratio=100:1) and $N_2$ as carrier gas. A 100 m CP-SIL 88 highly polar capillary column with an internal diameter of 0.25 mm and a film thickness of 0.2 μm was used for separation. Initially, the column temperature is kept at 180° C. for 50 min, and then raised at 10° C./min to 225° C. and held there for 15 min. The FID detector used was kept at 280° C. Heptadecane was used as internal standard. Most CLA isomers were identified based on retention times, using references from Matreya LLC. Other CLA isomers were identified based on literature data.

Example 1

Preparation & Characterisation of Heterogeneous Ru-USY Catalysts 0.5 wt % Ru was introduced in a commercial USY zeolite (CBV780, Zeolyst) via ion-exchange. The ion-exchange was performed under stirring for 24 h at room temperature of the zeolite in water slurry, containing the required amount of Ru-precursor ($Ru(NH_3)_6Cl_3$) in a 200 mL aqueous solution per gram of dry zeolite.

Prior to metal loading, the H-USY zeolite was brought to the $NH_4$-form via a room temperature ion-exchange step lasting for 2-16 h, using a 200 mL aqueous $NH_3$ ($NH_4OH$) solution of 0.0015, 0.0030 or 0.0150 M per gram of dry zeolite.

In order to obtain the Ru/Na-USY catalyst, the $NH_4$-USY zeolite was brought in the Na-form via two successive room temperature ion-exchange steps lasting for 16 h, before metal loading. Two hundred milliliters of an aqueous 1 M NaCl solution per gram of dry zeolite was used.

In order to obtain the Ru/Cs-USY catalyst, the Na-USY zeolite was brought in the Cs-form via two successive room temperature ion-exchange steps lasting for 48 and 72 h, respectively, before metal loading. 25 mL of an aqueous 0.1 M Cs-acetate solution per gram of dry zeolite was used.

After each exchange, the filtration residue is washed three times with distilled water and dried at 100° C. Except after the Ru exchange, the zeolite was dried at 50° C. in order to inhibit metal clustering.

The metal content of the exchange solution after reaction was determined by Inductively Coupled Plasma Atomic Absorbance (ICP-AA). No Ru could be detected after Ru ion-exchange of the zeolite samples which were exchanged with 0.0030 and 0.0150 M $NH_4OH$, while a very low Ru level (25 mg/L), corresponding to a final Ru loading of 0.47 instead of 0.50 wt %, was measured for the zeolite sample exchanged with 0.0015 M NH$_4$OH.

Ru-loaded catalysts are activated by a two- or three-step process. Prior to activation, the dry powders were compressed, crushed and sieved, the 0.25-0.50 mm fraction being retained for further use.

In the two step activation process, the Ru-complex was broken down by two heating steps under flowing nitrogen (120 mL/g/min): from room temperature to 200° C. applying a heating rate of 2° C./min and then from 200 to 300° C. applying a heating rate of 3° C./min. This way, H$_2$-free Ru-catalysts were obtained.

In the three step activation process, the two heating steps were followed by a reduction of the Ru-ions under flowing hydrogen (120 mL/g/min) at 400° C. (5° C./min).

In addition to catalysts with Ru load of 0.5 wt %, also catalysts with Ru loads of 0.25 wt %, 1.0 wt % and 1.37 wt % were synthesized.

Figure 1:
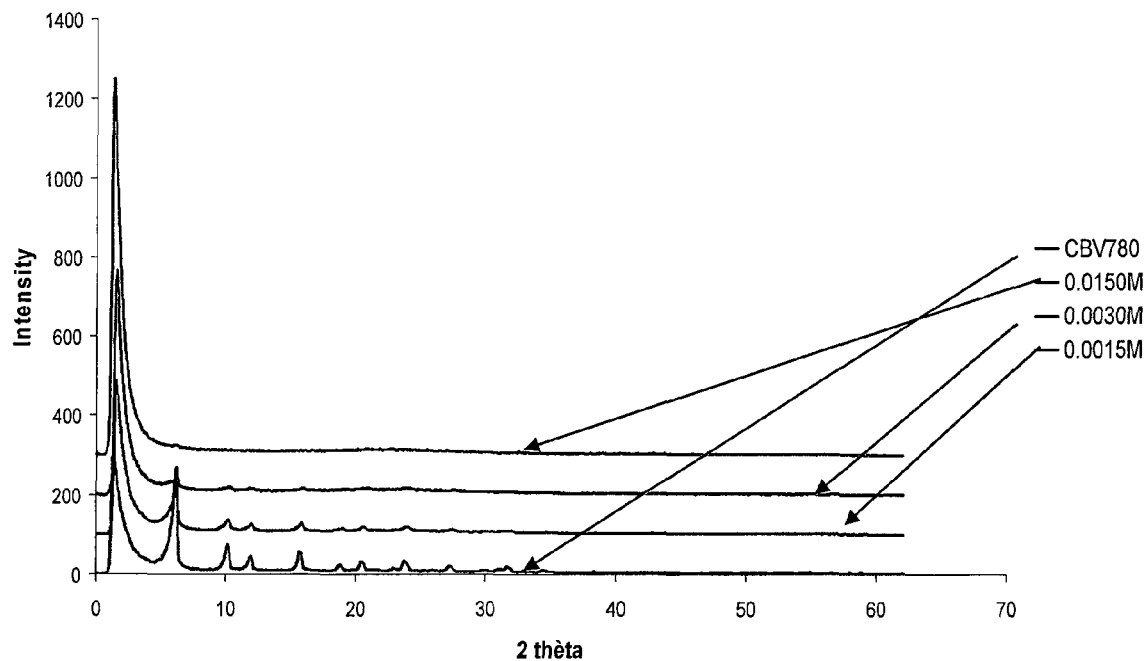
FIG. 1 shows XRD patterns of parent (H-USY, CBV780) and $NH_4OH$-treated H-USY zeolite samples.

The X-ray diffraction patterns of the parent (CBV780) and NH$_4$OH treated USY zeolites clearly show a gradual decrease in crystallinity with the concentration of the NH$_4$OH solution (FIG. 1). The intensities of the NH$_4$OH-treated crystals decrease and even disappear: a higher concentration of NH$_4$OH thus leads to a more severe impact on the micropore structure of the zeolite. Furthermore, only very small Ru-clusters (around 1 nm) could be detected in the Ru/H-USY (treated with 0.0015 M NH$_4$OH solution) catalyst, whereas no Ru-clusters could be detected in the Ru/H-USY (treated with 0.015M NH$_4$OH solution) catalyst (data not shown).

The CO-chemisorption measurements clearly indicate that a higher concentration of the NH$_4$OH treatment leads to a higher Ru dispersion in the final Ru/USY catalyst (Table 1). The Ru-dispersion of the Ru/Na-USY and Ru/Cs-USY catalysts are even higher than that of the Ru/H-USY catalyst, obtained by the same NH$_4$OH-treatment.

TABLE 1

Ru-dispersions of the different Ru/USY catalysts obtained by CO chemisorption, assuming a Ru/CO ratio of 1.

| Catalyst | Ru-dispersion (%) |
|---|---|
| Ru/H-USY (0.0015M) | 45 |
| Ru/H-USY (0.0150M) | 72 |
| Ru/Na-USY (0.0150M) | 88 |
| Ru/Cs-USY (0.0150M) | 87 |

Figure 5:
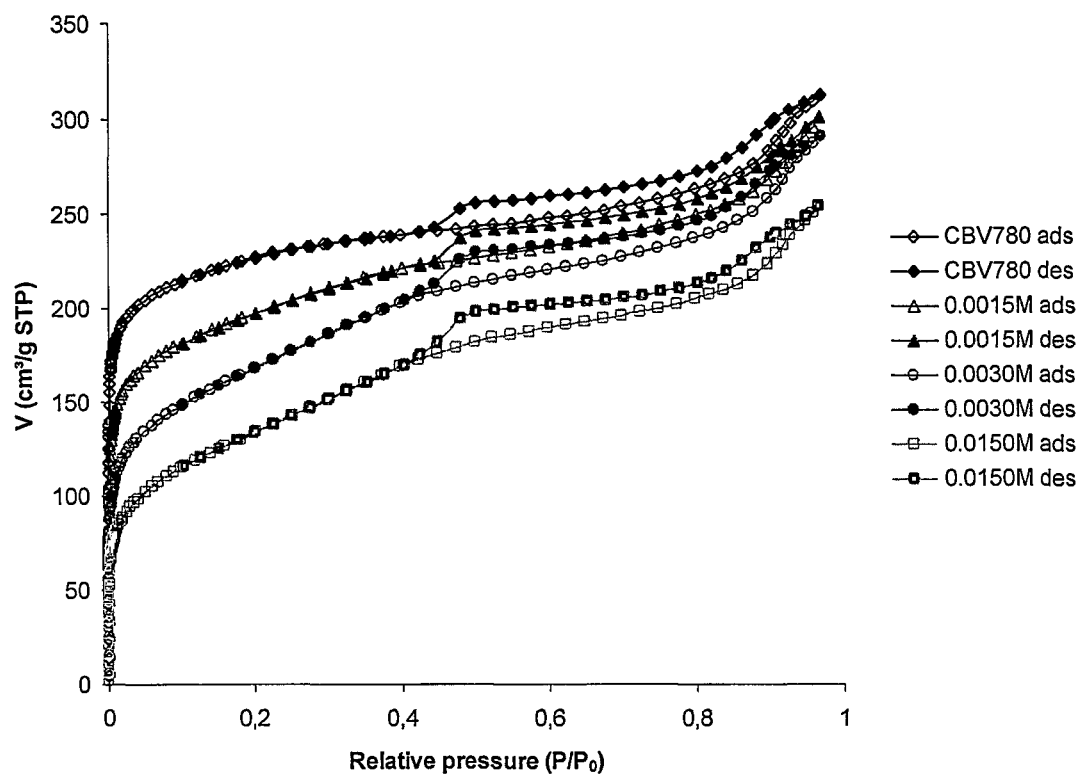
FIG. 5 shows the nitrogen sorption isotherms of the parent USY (CBV780) and $NH_4OH$-treated USY samples.
Figure 6:
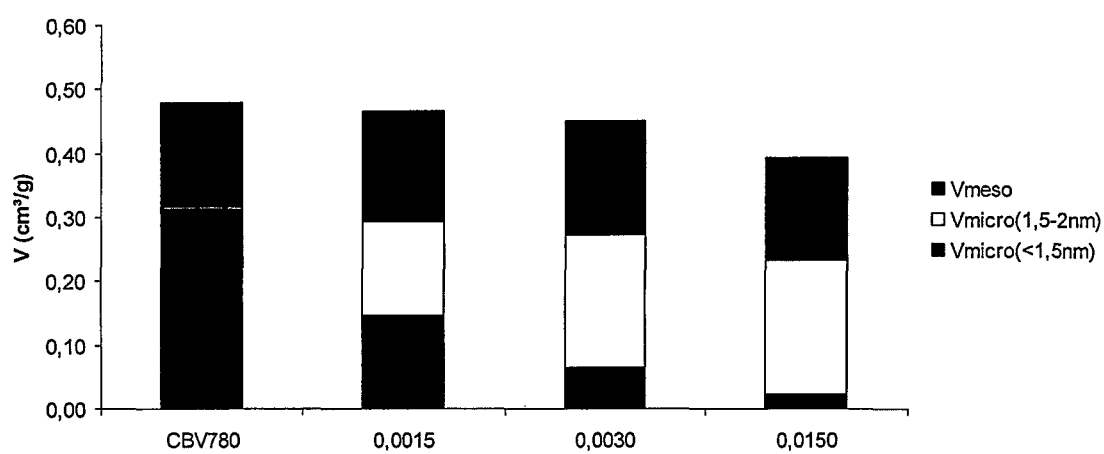
FIG. 6 shows the small micropore (<1.5 nm), large micropore (1.5-2 nm) and mesopore volume of the parent H-USY zeolite (CBV780) and the $NH_4OH$-treated H-USY samples.

The CO chemisorption data clearly demonstrate that the NH$_4$OH treatment leads to an increased dispersion of the metal in the final Ru-catalyst. Without being bound by theory, we believe this may be due to an increased large micropore and/or small mesopore volume with a concomitant decreased small micropore volume. FIG. 5 and FIG. 6 clearly indicate that the small micropore volume decreases gradually with increasing concentration of the NH$_4$OH-treatment, while the large micropore volume increases as a consequence of the NH$_4$OH-treatment. The loss in small micropore volume is in line with the partial damage of the crystal structure (FIG. 1). The BJH mesopore size distribution, as presented in FIGS. 7A and 7B, reveals that the large micropores and/or small mesopores created by the NH$_4$OH-treatment are centred around 1.5-4 nm, whereas the large mesopores already present in the parent USY zeolite are much larger (20-30 nm) and remain unaffected.

Example 2

Isomerisation—Influence of Type of Support & Counterion

Different zeolite supports were loaded with ruthenium and tested in the isomerisation of methyl linoleate (Ru/ML=4 wt %) (Table 2). The zeolites tested differ in topology (MFI (ZSM-5), BEA (BETA), FAU (Y)), Si/Al ratio (2.5-180) and counter cation (H$^+$, Na$^+$, Cs$^+$). The results of a commercial Ru/C catalyst are incorporated as reference.

During the isomerisation of methyl linoleate four types of products are formed, viz. conjugated (CLA) and non-conjugated C18:2 isomers (NC), hydrogenated products (HP) and coke (CP), remaining on the catalyst and thus detected as deficiency in the carbon mass balance. The formation of conjugated and non-conjugated C18:2 isomers is equilibrium limited, whereas the formation of hydrogenated products and coke is irreversible. The selectivity for the different product classes as well as for the beneficial CLA isomers viz. c9,t11-+t10,c12-CLA ($S_{ct}$), and t9,t11-+t10,t12-CLA ($S_{tt}$), at comparable conversions is given in Table 2 for all catalysts.

TABLE 2

Catalytic properties of supported ruthenium catalysts for the isomerisation of methyl linoleate (ML).

| | Support | Si/Al | $A_i^{[b]} \times 10^{-5}$ [mol·min$^{-1}$] | Time [min] | $X_{ML}^c$ [%] | $Y_{CLA}^d$ [wt %] | $S_{CLA}^e$ [%] | $S_{ct}^f$ [%] | $S_{tt}^g$ [%] | $S_{HP}^h$ [%] | $S_{NC}^i$ [%] | $S_{CP}^j$ [%] |
|---|---|---|---|---|---|---|---|---|---|---|---|---|
| 1 | C | / | 0.18 | 240 | 58 | 37 | 63 | 30 | 24 | 3 | 22 | 13 |
| 2 | H-ZSM5 | 140 | 1.54 | 15 | 68 | 20 | 29 | 3 | 11 | 0 | 17 | 53 |
| 3 | Na-ZSM5 | 140 | 0.32 | 240 | 74 | 35 | 48 | 6 | 19 | 3 | 17 | 32 |
| 4 | Cs-ZSM5 | 140 | 0.16 | 240 | 54 | 27 | 49 | 11 | 18 | 2 | 25 | 25 |
| 5 | H-BETA | 180 | 1.74 | 15 | 77 | 36 | 47 | 5 | 17 | 2 | 24 | 27 |
| 6 | Cs-BETA | 180 | 0.57 | 60 | 69 | 46 | 67 | 13 | 36 | 2 | 21 | 10 |
| 7 | H—Y | 2.5 | 2.27 | 15 | 100 | 0 | 0 | 0 | 0 | 0 | 0 | 100 |
| 8 | Na—Y | 2.5 | 2.27 | 15 | 100 | 0 | 0 | 0 | 0 | 0 | 0 | 100 |
| 9 | H-USY | 15 | 2.27 | 15 | 100 | 0 | 0 | 0 | 0 | 0 | 0 | 100 |
| 10 | Na-USY | 15 | 2.27 | 15 | 100 | 0 | 0 | 0 | 0 | 0 | 0 | 100 |
| 11 | H-USY | 30 | 2.27 | 15 | 100 | 0 | 0 | 0 | 0 | 0 | 0 | 100 |
| 12 | H-USY | 40 | 1.29 | 30 | 73 | 33 | 45 | 4 | 16 | 12 | 30 | 13 |

TABLE 2-continued

Catalytic properties of supported ruthenium catalysts for the isomerisation of methyl linoleate (ML).

| | Support | Si/Al | $A_i^{[b]} \times 10^{-5}$ [mol·min$^{-1}$] | Time [min] | $X_{ML}^c$ [%] | $Y_{CLA}^d$ [wt %] | $S_{CLA}^e$ [%] | $S_{ct}^f$ [%] | $S_{tt}^g$ [%] | $S_{HP}^h$ [%] | $S_{NC}^i$ [%] | $S_{CP}^j$ [%] |
|---|---|---|---|---|---|---|---|---|---|---|---|---|
| 13 | Na-USY | 40 | 0.95 | 30 | 74 | 46 | 62 | 7 | 23 | 2 | 14 | 22 |
| 14 | Cs-USY | 40 | 0.86 | 30 | 82 | 67 | 82 | 10 | 31 | 1 | 9 | 9 |

[b]initial activity (after 15 min);
$^c$conversion of methyl linoleate;
$^d$yield of CLA;
$^e$selectivity for total CLA;
$^f$selectivity for c9,t11 + t10,c12 CLA;
$^g$selectivity for t9,t11 + t10,t12 CLA;
$^h$selectivity for hydrogenation products (C18:1 + C18:0);
$^i$selectivity for non-conjugated C18:2 isomers;
$^j$selectivity for catalyst adsorbed material (coke) (deficiency of carbon mass balance).

The type of support seem to have a large influence on both methyl linoleate conversion and CLA selectivity. Zeolites Y and USY with Si/Al ratio≤30, do not show any CLAs formation, irrespective of the counter cation present in the zeolite lattice (Table 2, entries 7-11). In all cases the conversion is very high, as after 15 minutes of reaction all methyl linoleate has disappeared. The products, collectively denoted as hydrocarbon coke (CP), remain strongly adsorbed on the catalyst surface. Reaction simulation in a thermobalance indicated that all reactant remained adsorbed on the catalyst support. Without being bound by theory, these observations can be explained by the high acid density of such zeolites. It is known that olefins can undergo proton catalyzed reactions on acid sites, such as isomerisation, polymerisation and cyclisation, polymerization products being trapped in the pore system of the support. Furthermore, it has already been shown that also CLAs can polymerize on Ru catalysts. Also Na-exchanged Y and USY zeolites with low Si/Al ratio show coke formation (Table 2, entries 7-10), caused by protons produced during the reduction of ion exchanged Ru(III)hexamine.

With Ru/USY catalysts having a Si/Al ratio of 40, CLAs were identified in the reaction mixture (Table 2, entries 12-14). Furthermore, the activity of these catalysts is much higher compared to the Ru/C catalyst, viz. 1.29 and 0.18× $10^{-5}$ mol/min for Ru/H-USY(40) and Ru/C, respectively.

Also, zeolite topology has an influence on the reaction characteristics. Comparison of Ru/H-ZSM-5, Ru/H-BETA and Ru/H-USY(40) reveal that at comparable conversion zeolite BETA (with small crystallites) and USY (with mesopores), show a higher selectivity for CLA formation (29, 45 and 47%, respectively (Table 2, entries 2, 5, 12). It should be stressed that the small pores of ZSM-5 show a higher reactivity for coke formation. Probably, the reactive conjugated products either undergo slow intraporous polymerisation or just block these pores. On the three catalysts, the nature of the products is the same, though the individual selectivities are different. Among the BETA and USY topology, the individual CLA selectivity is comparable, pointing that for the more open zeolite lattices pore architecture is not a selectivity dominating parameter.

The use of different counter cations ($H^+$, $Na^+$, $Cs^+$) in the ZSM-5 support has a large influence on the activity (Table 2, entries 2-4), activities of Ru/Cs-ZSM-5 and Ru/Na-ZSM-5 being reduced compared to Ru/H-ZSM-5, the former sample showing the lowest activity, comparable with that of Ru/C. As the presence of bulky $Cs^+$ ions rather than the nature of the charge compensating cations, viz. $Na^+$ and $Cs^+$, affect overall catalyst behaviour, it seems that pore blocking in ZSM-5 with larger cations could be at the basis of the reduced activity. An effect of the nature of the charge compensating cations is also encountered with BETA (Table 2, entries 5,6) and USY(40) samples (Table 2, entries 12-14), mainly at the level of the CLA selectivity. More basic Cs-catalysts show an enhanced selectivity for CLA formation, while acid catalysts seem to show enhanced activity for formation of coke ($H^+>Na^+>Cs^+$). The enhanced CLA yield and selectivity can presumably be attributed to changed properties of the Ru metal clusters under influence of the enhanced basicity of the lattice. It is expected that these changes occur at the level of the residual electron density on the clusters. The highest CLA selectivity is obtained with the Ru/Cs-USY(40) catalyst, viz. 82% at a conversion of 82% (Table 2, entry 14), which is much higher than that of the Ru/C catalyst, viz. 63% at a conversion of 58% (Table 2, entry 1). Important to mention is that Ru/Cs-USY shows very low selectivity for hydrogenated products, due to the absence of a hydrogen donor. In addition, compared to literature, the Ru/Cs-USY catalyst in a $H_2$ free atmosphere yields a much higher CLA productivity and specific yield. Similar results were obtained both with a $H_2$ activated catalyst as with the $H_2$ free catalysts. Thus, to our surprise, even without $H_2$ activation or without a source of $H_2$ in the reaction medium, the Ru/Cs-USY catalyst efficiently catalyses the conversion of methyl linoleate to CLA.

Example 3

Catalyst Characterisation—Determination of Active Sites

As discussed in Example 2, it appears that superior CLA production occurred with the Ru/Cs-USY(Si/Al 40) catalyst. NMR measurements of the solvent, viz. n-decane, after reaction, reveal that the solvent is inert under reaction conditions. In order to identify the active centres responsible for the isomerisation reaction, tests were performed using Cs-USY (40) devoid of Ru. After 1 h of reaction, a CLA yield of only 1 wt % and a conversion of 5 wt % is obtained, compared to a CLA yield of 75 wt % and a conversion of 94 wt % for added Ru (Table 3, entries 1,2). Hence, the ML isomerisation activity towards CLAs can be assigned to the presence of Ru.

Ru-dispersion from CO-chemisorption was very high, viz. 87%, pointing to the presence of highly dispersed Ru. ML isomerisation activity of such highly dispersed Ru was not known.

As described in the experimental section, $Ru(NH_3)_6^{3+}$-exchanged zeolite is first heated under $N_2$-flow till 350° C. MS analysis of the decomposition gases reveals loss of $H_2O$ (from room temperature till 150° C.) and $NH_3$ (from 220 till 350° C.), corresponding to zeolite dehydration and decomposition of the Ru-complex. In a further optional step, the catalyst is reduced under flowing $H_2$ at 400° C. (5° C./min). Experimentally, it was indeed confirmed that by omission of the reduction step, also high conversions were obtained, although the CLA yield decreases from 75 to 55 wt % (Table 3, entries 2,3). Hence, no hydrogen is required when highly-dispersed Ru/USY catalysts are used for the production of CLA, nor in the pre-treatment procedure of the catalyst, nor during the isomerisation reaction.

TABLE 3

Isomerisation of methyl linoleate with various USY(40) catalysts, using different activation procedures[a].

| Entry | Catalyst | activation | $X_{ML}$ [wt %] | $Y_{CLA}$ [wt %] | $Y_{NC}$ [wt %] | $Y_{HP}$ [wt %] | $Y_{CP}$ [wt' %] |
|---|---|---|---|---|---|---|---|
| 1 | Cs/USY | $N_2/H_2/air$[b] | 5 | 1 | 0 | 0 | 3 |
| 2 | Ru/Cs-USY | $N_2/H_2/air$[b] | 94 | 75 | 10 | 2 | 5 |
| 3 | Ru/Cs-USY | $N_2/air$ | 83 | 55 | 19 | 3 | 5 |
| 4 | Ru/Cs-USY | $N_2/O_2/air$[c] | 85 | 57 | 15 | 2 | 9 |
| 5 | Ru/Cs-USY | $N_2/H_2$[d] | 100 | 55 | 20 | 7 | 15 |

[a]Reaction conditions: 165° C., [ML] = 7 mmol/L, 0.8 g (0.5Ru/)USY(40), 60 min; abbreviations of Table 2;
[b]under $N_2$ and $H_2$ up to 350° C. and 400° C., respectively, followed by room temperature transfer from flow to batch reactor in air;
[c]under $N_2$ up to 350° C., followed by room temperature contact with flowing $O_2$;
[d]transfer of reduced catalyst from flow to batch reactor in inert conditions;
[e]under $N_2$ up to 350° C., followed by room temperature contact with flowing $NH_3$.

From a previous report it is known, that highly dispersed nano-sized metallic Ru clusters in zeolite Y, are easily oxidized at room temperature. This was confirmed with the Ru/Cs-USY catalyst, by means of an $O_2$ titration experiment at room temperature, immediately after the activation procedure, without making contact with air. The high uptake of $O_2$ at room temperature proves that metallic Ru is rapidly converted to $RuO_2$.

The results of the ML isomerisation reaction using a Ru/Cs-USY(40) catalyst, which was contacted with a $O_2$-flow (2 mL/s/g) for 60 minutes (Table 3, entry 4), shows no activity nor selectivity differences with a catalyst which did not receive such treatment (Table 3, entry 3). Therefore, in both cases the presence of highly dispersed $RuO_2$ should be present at least at the moment the catalyst is added to the batch reactor. If the catalyst was not contacted with air before the reaction, and hence the Ru-species were fully reduced before reaction, also high activity for ML conversion was observed (Table 3, entry 5) with a somewhat higher selectivity for hydrogenated and non-conjugated C18:2 isomers. Indeed, with this catalyst, more hydrogen is available on the catalyst surface, leading to enhanced consecutive isomerisation and hydrogenation.

Example 4

Isomerisation—Influence of Catalyst Activation Conditions

From the above results it follows that a nitrogen activated Ru/Cs-USY catalyst is oxygen sensitive. Although a somewhat lower activity is obtained, the formation of $RuO_2$ species on the catalyst has a positive influence on the CLA yield. In contrast, literature concludes that the formation of $RuO_2$ species during the decomposition step, by using $O_2$ instead of $N_2$, greatly influences the Ru dispersion, as upon reduction, large Ru clusters are formed on the external surface of the zeolite. Indeed, transmission electron microscopy images clearly show the presence of large Ru-clusters on the external crystal surface of the $O_2^-$ pretreated catalyst (up to 50-200 nm) (data not shown). In contrast to the $N_2$-activated sample, these clusters contain only metallic Ru (data not shown). The Ru-dispersion, calculated from CO-chemisorption measurements, of the $O_2$-activated sample (after reduction) is only 4%, whereas the $N_2$-pretreated sample has a Ru-dispersion of 87%. The performance of both catalysts in the ML isomerisation reaction is compared at similar conversion in Table 4.

TABLE 4

Performance of a $N_2$ and $O_2$-pretreated Ru/Cs-USY(40) catalyst in the isomerisation of methyl linoleate[a].

| Activation | $D_{Ru}$[b] [%] | $A_i$[c] [×10$^{-5}$ mol·min$^{-1}$] | Time [min] | $X_{ML}$ [%] | $Y_{CLA}$ [wt %] | $S_{CLA}$ [%] | $S_{ct}$ [%] | $S_{tt}$ [%] | $S_{NC}$ [%] | $S_{HP}$ [%] | $S_{CP}$ [%] |
|---|---|---|---|---|---|---|---|---|---|---|---|
| $N_2/H_2/air$[d] | 87 | 19.24 | 120 | 82 | 67 | 82 | 44 | 30 | 6 | 1 | 11 |
| $O_2/H_2/air$ | 4 | 3.40 | 480 | 83 | 19 | 23 | 3 | 11 | 35 | 2 | 39 |

[a]Reaction conditions: T = 165° C., [ML] = 350 mmol/L, 0.8 g 0.5Ru/Cs-USY(40), abbreviations see Table 1;
[b]Ru metal dispersion from CO measurements for in situ pretreated samples;
[c]activity after 15 min of reaction;
[d]same as Table 4, entry 2.

Not only is the $N_2$-pretreated catalyst much more active, but also shows a much higher selectivity for CLAs formation, while the $O_2$-pretreated catalyst has a higher selectivity towards non-conjugated C18:2 isomers (NC) and coke (CP). Hence, it seems obvious that small Ru-oxide species, obtained after pretreatment in inert atmosphere followed by room temperature exposure to air, should be the active sites for CLAs formation. Larger Ru metal clusters obtained after oxygen activation and subsequent reduction are not sensitive to room temperature air contact and should lead to higher levels of undesired non-conjugated C18:2 isomers.

Interestingly, the Ru-cluster size, has also an influence on the CLA isomer distribution. Smaller Ru(-oxide) clusters (decomposition under $N_2$) show an enhanced selectivity for the formation of c9,t11- and t10,c12-CLA isomers compared to the larger Ru clusters (decomposition under $O_2$). With the $N_2$-activated catalyst, the c9,t11- and t10,c12-isomers are initially the dominantly formed CLA isomers. After longer reaction times, the latter isomers are mainly converted to the thermodynamically more stable t9,t11- and t10,t12-CLA isomers, whereas only minimal positional isomerisation is observed after 6 h of reaction. With the $O_2$-activated catalyst, both the c9,t11+t10,c12- and t9,t11+t10,t12 CLA levels decrease after longer reaction times. Simultaneously, the concentration of other positional CLA isomers increases.

Concluding, it is not necessary to invoke the presence of $RuO_2$ clusters for CLAs formation and the occurrence of a carbanion mechanism. The favourable effect of small Ru-metal particle sizes for CLAs selectivity is obvious.

Example 5

Isomerisation—Influence of Methyl Linoleate Concentration

The influence of the methyl linoleate (ML) concentration on the reaction characteristics of ML isomerisation with a Ru/Cs-USY(40) catalyst was investigated. Indeed, in order to obtain a process with a high productivity and specific yield, and hence to make the process industrially attractive and sustainable, it is important that the catalyst is able to convert methyl linoleate to CLAs in a reaction with a low Ru/ML ratio with a high selectivity and activity. In Table 5 the activity and the different selectivities towards the formation of CLAs, non-conjugated C18:2 isomers, hydrogenated products and cokes at maximum CLA yield are compared (Table 5, entries 1-4).

It is shown that the activity rises as the methyl linoleate concentration is increased from 7 to 350 mmol/L. This leads to a very significant increase in productivity and specific yield, the productivity at maximum CLA yield increases from 0.029 to 0.391 g $CLA.L^{-1}.min^{-1}$ and the specific yield from 17 to 234 g $CLA.g\ Ru^{-1}.h^{-1}$.

tion of trans,trans and unconjugated CLAs. For lower initial ML concentration the equilibrium is reached at lower ML conversion. The data allow to determine the 9,11 and 10,12 CLA product distribution at equilibrium, viz. total cis,trans of 27.5%, total trans,trans of 65.5%, and total cis,cis of 7%. The level of other positional CLA isomers increases with conversion and is higher for lower ML concentrations. At equilibrium around 45% of the total CLA isomers are present as CLAs with double bonds on positions different from 9,11 and 10,12.

From these observations it can be concluded that the initially kinetically formed c9,t11- and t10,c12 CLA isomers are converted to the thermodynamically more stable t9,t11- and t10,t12-CLA isomers and the 9,11 and 10,12 isomers are converted to other positional CLAs for longer reaction times. Both phenomena are enhanced for reduced methyl linoleate concentration.

Example 6

Isomerisation—Influence of the Nature of the Counter-Ion in Ru/USY(40)

Owing to the positive influence of a low Ru/ML ratio on the reaction characteristics, Ru/H-USY, Ru/Na-USY and Ru/Cs-USY catalysts were tested in the isomerisation of a more concentrated methyl linoleate solution, viz. [ML]=350 mmol/L. With each catalyst, much higher productivities, specific yields and selectivities towards the desirable CLA isomers were obtained compared to the respective reactions with a low methyl linoleate concentration (7 mmol/L). Comparison of the three catalysts at [ML]=350 mmol/L, shows that

TABLE 5

Influence of the methyl linoleate concentration on the performance of the Ru/USY(40) catalyst in the isomerisation of methyl linoleate[a]. Results are given for maximal CLA yield.

| Entry | Counter cation | [ML] [mmol/L] | $A_i$ [×$10^{-5}$ mol · $min^{-1}$] | $X_{ML}$ [%] | Time [min] | $Y_{CLA}$ [wt %] | P [g(CLA)$L^{-1}min^{-1}$] | TOF [$h^{-1}$] |
|---|---|---|---|---|---|---|---|---|
| 1 | Cs | 7 | 0.86 | 94 | 60 | 69 | 0.029 | 8.1 |
| 2 | Cs | 21 | 2.85 | 92 | 60 | 74 | 0.093 | 23.7 |
| 3 | Cs | 70 | 12.25 | 92 | 60 | 77 | 0.289 | 78.9 |
| 4 | Cs | 350 | 19.24 | 93 | 240 | 75 | 0.391 | 99.8 |
| 5 | H | 7 | 1.29 | 73 | 30 | 33 | 0.028 | 12.5 |
| 6 | H | 350 | 14.72 | 81 | 360 | 40 | 0.139 | 57.9 |
| 7 | Na | 7 | 0.95 | 93 | 60 | 47 | 0.020 | 8.0 |
| 8 | Na | 350 | 11.32 | 81 | 360 | 68 | 0.236 | 57.9 |

[a]Reaction conditions: 165° C., 0.8 g 0.5Ru/USY(40);
[b] mol ML converted per mol Ru and per h.

Figure 3A:
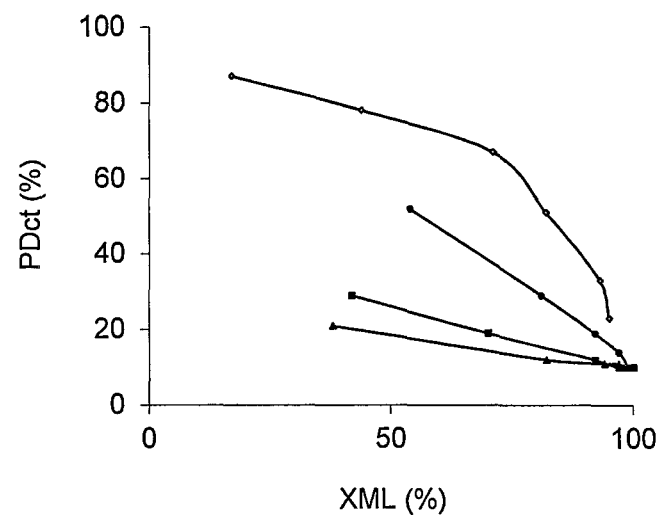
FIG. 3 shows the influence of the Ru/ML ratio on the CLA isomer product distribution (PD) during the isomerisation of methyl linoleate using a Ru/Cs-USY(40) catalyst: (A) $PD_{ct}$ (c9t11+t10c12-CLA), (B) $PD_{tt}$ (t9t11+t10t12 CLA), (C) $PD_{other\ CLA}$ (other positional CLA isomers); ▲ [ML]=7 mmol/L, ■ [ML]=21 mmol/L, ● [ML]=70 mmol/L, ◊ [ML]=350 mmol/L.
Figure 3B:
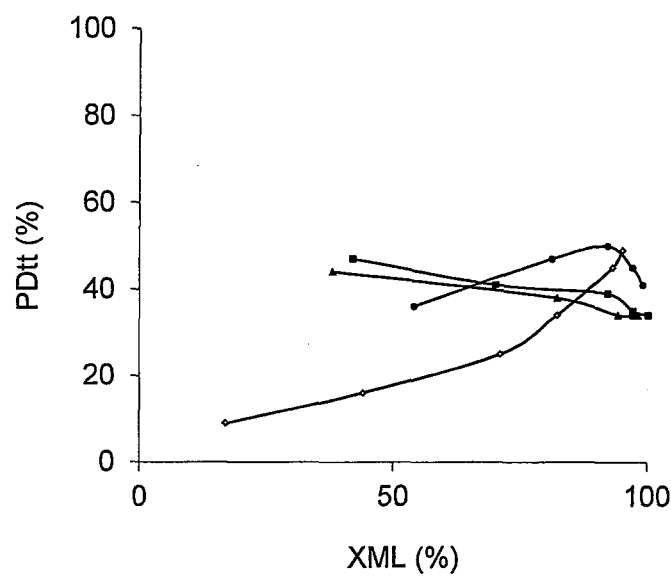
Figure 3C:
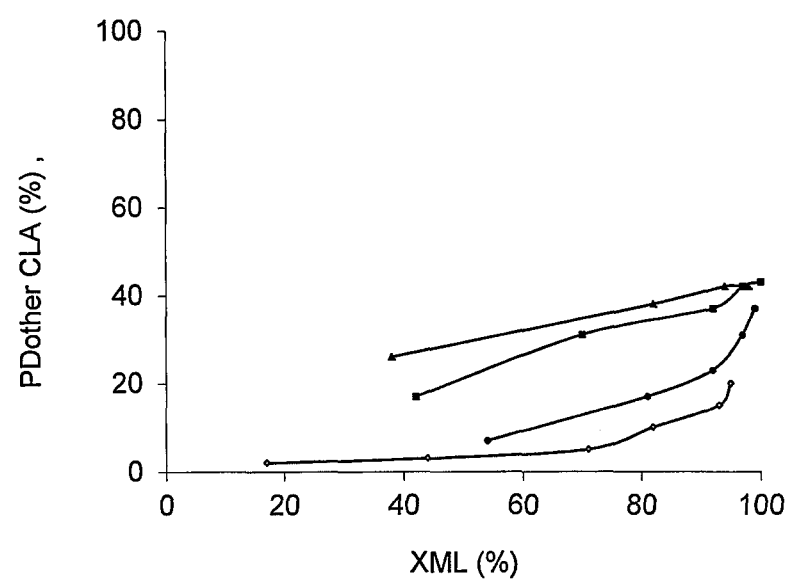
Figure 4A:
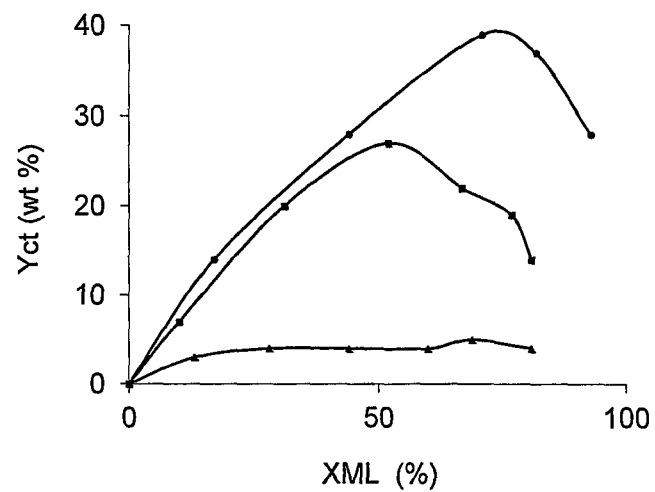
FIG. 4 shows the influence of the counter cation on the yield of conjugated and non-conjugated C18:2 isomers during the isomerisation of methyl linoleate with (▲) Ru/H-USY (40), (■) Ru/Na-USY(40) or (●) Ru/Cs-USY(40). Reaction conditions: 165° C., [ML]=350 mmol/L.
Figure 4A:
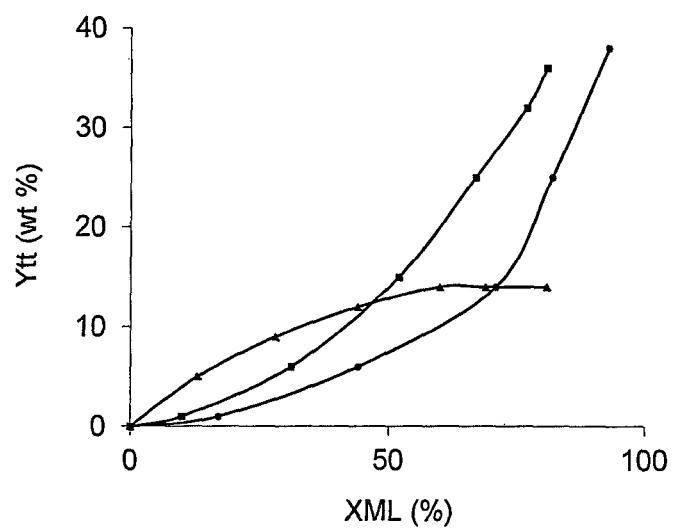
Figure 4B:
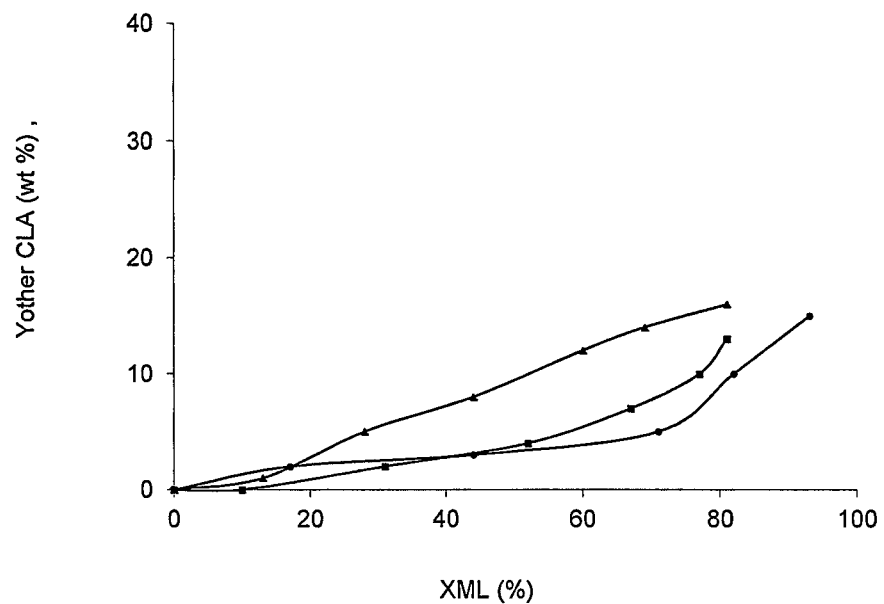
Figure 4B:
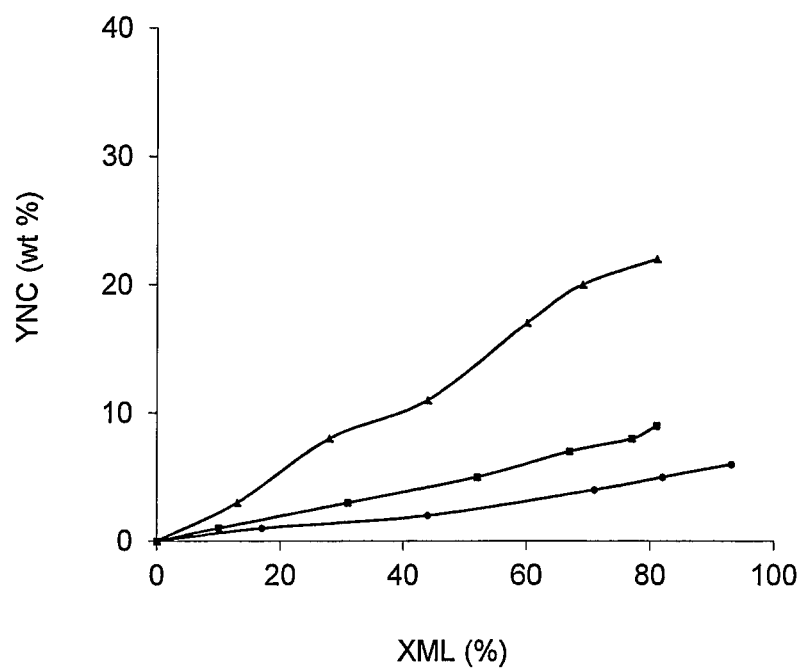

These values are much higher compared to other heterogeneous processes found in literature and are comparable to the homogeneous process, today used industrially. The selectivity for the different products (CLA, non-conjugated CLA, hydrogenated products and coke) remains rather unaffected by the ML concentration. In contrast, the CLA isomer distribution in function of the conversion is largely influenced by the Ru/ML ratio (FIG. 3). Initially, the contribution of the c9,t11- and t10,c12-isomers is high and at high ML conversion levels off at around 10%. The contribution of these beneficial isomers among all CLAs increases with higher methyl linoleate levels. Also the fraction of the t9,t11- and t10,t12-CLA isomers shows the same behaviour when plotted against conversion. Its contribution points to values around 35% for higher ML levels. It is clear at least for the high ML concentrations that cis,trans (trans,cis) isomers are the primary CLA product isomers, followed by consecutive formathe Ru/Cs-USY catalyst gives the highest CLA yield and hence also the highest productivity and turn-over frequency (TOF) (Table 5, entries 4, 6, 8). The obtained TOFs are considerably higher than those calculated from literature.

Furthermore, the Ru/Cs-USY catalyst shows the highest selectivity for desirable c9,t11- and t10,c12-CLA isomers (FIG. 4). With the acid Ru/H-USY catalyst faster isomerisation towards the thermodynamically more stable trans,trans-CLAs takes place as well as positional isomerisation of the 9,11 and 10,12-isomers to both conjugated and non-conjugated C18:2 isomers. The more basic Na- and Cs-exchanged USY catalysts show a much lower initial activity for formation of t9,t11- and t10,t12-CLA isomers and other positional CLA isomers. Only at higher conversions (around 50% for Ru/Na-USY and around 70% for Ru/Cs-USY), the c9,t11- and t10,c12 CLA isomers are converted to their respective geometrical trans,trans isomers and other positional CLA isomers. The level of non-conjugated C18:2 isomers only slightly increases with conversion.

Example 7

Catalyst Regeneration

Figure 2:
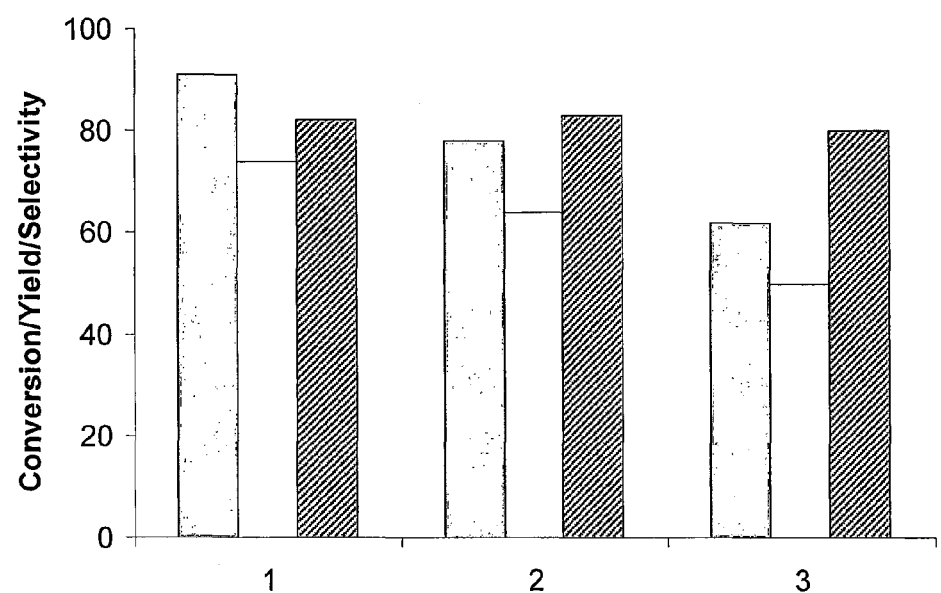
FIG. 2 shows a recycling experiment using Ru/Cs-USY (40), 300 min of reaction (gray=conversion of methyl linoleate, white=yield of CLA, pattern=selectivity towards CLA) ([ML]=350 mmol/L).

The Ru/Cs-USY(40) catalyst was tested in a recycling experiment. After the first run, the catalyst was filtered and washed with dioxane. After drying overnight at room temperature, the catalyst was directly tested in a second run, without any further pre-treatment. In the same way, also a third run was performed. The conversion and CLA yield of the three runs are compared in FIG. 2. It can be concluded that, although there is some loss in activity, probably caused by loss of active sites as a result of coke formation, the Ru/Cs-USY catalyst remains very selective in the isomerisation of methyl linoleate.

Example 8

Isomerization of Vegetable Oils

Isomerisation reactions were carried out in a 100-mL Parr-autoclave. Typically, 40 g of oil, such as safflower oil or soy oil, was loaded together with the catalyst (0.8 g of a 0.5 wt % Ru-USY catalyst, corresponding to a Ru/lipid ratio of 0.01 wt %). The reaction mixture was stirred mechanically at 500 rpm. After flushing the reaction mixture with $N_2$, the temperature was raised to the reaction temperature (120-180° C., typically 180° C.). Samples were withdrawn from the reactor at certain time intervals to follow the reaction progress over time.

The fatty acid composition of the samples was determined by analyzing the corresponding fatty acid methyl esters (FAMEs) by gas chromatography as described in Example 2.

FIGS. 8 and 9 show the conversion of linoleate and the cis-9,trans-11 and trans-10,cis-12 CLA yield of different Ru/H-USY (Si/Al=40) catalysts during the isomerisation of safflower oil. It is clear that the creation of a more open pore system and a high Ru-dispersion, by treating the parent H-USY zeolite with diluted $NH_4OH$ concentrations, has a positive influence on the activity and the selectivity towards the desirable CLA isomers.

FIGS. 10 and 11 compare the performance of the Ru/H-USY and the Ru/Cs-USY catalysts in the isomerisation of safflower oil. Both catalysts were prepared by treating the parent USY (CBV780) zeolite with 0.0150 M $NH_4OH$.

Table 6 shows the isomerization of safflower oil in the absence of solvents. The Ru catalyst is able to efficiently and selectively convert linoleic acid in the glyceride to CLA, particularly c9,t11- and t10,c12-CLA. Unwanted hydrogenated byproducts, particularly C18:1 remains low. Similar results were obtained for soy and sunflower oil.

TABLE 6

Isomerisation of safflower oil using a 0.5 wt % Ru/Cs-USY catalyst, prepared by treating the parent USY zeolite with 0.0150M $NH_4OH$ (Ru/lipid = 0.01 wt %) at 180° C. under $N_2$ atmosphere.

| Time (min) | Conversion of LA (%) | Hydrogenation (%) | CLA (wt %) | c9t11 + t10c12 (wt %) | C18:1 trans |
|---|---|---|---|---|---|
| 30 | 3.6 | 0.0 | 2.7 | 2.2 | 0.0 |
| 75 | 7.9 | 0.2 | 5.8 | 4.3 | 0.4 |
| 120 | 10.1 | 0.4 | 7.5 | 5.5 | 0.5 |
| 240 | 14.3 | 0.5 | 10.4 | 7.0 | 0.8 |
| 360 | 16.7 | 0.7 | 11.9 | 7.7 | 1.1 |
| 1440 | 28.2 | 2.7 | 19.2 | 9.8 | 2.8 |

Furthermore, compared to literature, our Ru/Cs-USY catalyst in a $H_2$ free atmosphere yields a much higher CLA productivity and specific yield even when the PUFA is present in a triglyceride (Table 7). In addition, formation of C18:1 trans fatty acids was very low, with typically tC18:1/CLA ratio of about 1:100.

The results presented, clearly show that, compared to other heterogeneous processes reported in literature, high productivities of and selectivities for CLA from methyl linoleate and oils rich in linoleic acid can be obtained via heterogeneous catalysis, when highly dispersed $RuO_2$ species are present in Si-rich USY catalysts at least when added to the batch reactor. When the reactions are performed in inert atmosphere, almost no hydrogenated products are formed.

Because of the very high productivities obtained with the Ru/Cs-USY(40) catalyst, this process can be a major breakthrough in the production of bio-based drying oils, paints and plastics. Moreover, as the beneficial CLA isomers are the main products with the Ru/Cs-USY catalyst, this research may also accelerate the development of CLA enriched functional foods.

TABLE 7

Hydrogenation/isomerisation of vegetable oils for high accumulation of CLA.

| Substrate | Catalyst | T (° C.) | P $H_2$ (bar) | Time (min) | CLA (mg/g oil) | c9t11 + t10c12 (mg/g oil) | C18:1 tr (wt %) | Spec Y. (gCLA/g metal · h) |
|---|---|---|---|---|---|---|---|---|
| Safflower | Ru/Cs-USY | 180 | / | 120 | 75 | 54 | 0.5 | 377 |
| Safflower | Ru/Cs-USY | 180 | / | 120 | 135 | 88 | 0.8 | 227 |
| Safflower | Ru/Cs-USY | 180 | / | 1440 | 279 | 112 | 4.9 | 39 |
| Soybean | Pricat 9910 (Ni) | 215 | 2.5 | 35 | 9 | 5 | ? | 9 [1] |
| Soybean | SP-7 (Ni) | 215 | 0.5 | 210 | 98 | 25 | ? | 6 [1] |
| Soybean | SP-7 (Ni) | 210 | 0.5 | 10 | 20 | 12 | 1.4 | 118 [2] |
| Soybean | SP-7 (Ni) | 210 | 0.5 | 180 | 163 | 39 | ? | 54 [2] |
| soybean | SP-7 (Ni) | 210 | 0.5 | 10 | 48 | 22 | 3.5 | 94 [3] |
| soybean | SP-7 (Ni) | 210 | 0.5 | 60 | 159 | 27 | 20.9 | 53 [3] |
| Soybean | N-545 (Ni) + S | 220 | 0.5 | 10 | 71 | 40 | 2.6 | 277 [4] |

TABLE 7-continued

Hydrogenation/isomerization of vegetable oils for high accumulation of CLA.

| Substrate | Catalyst | T (° C.) | P H$_2$ (bar) | Time (min) | CLA (mg/g oil) | c9t11 + t10c12 (mg/g oil) | C18:1 tr (wt %) | Spec Y. (gCLA/metal · h) |
|---|---|---|---|---|---|---|---|---|
| Soybean | N-545 (Ni) + S | 220 | 0.5 | 50 | 197 | 57 | 17.2 | 158 [4] |
| Safflower | Rh/Al_SBA_15 | 180 | 0.3 | 300 | 70 | 30 | 5 | 280 [5] |

[1] Jung & Ha, J. Agr. Food Chem. 1999, 47, 704-708;
[2] Jung et al., J. Agr. Food Chem. 2001, 49, 3010-3016;
[3] Jung et al., J. Am. Oil Chem. Soc. 2002, 79, 501-510;
[4] Ju & Jung, J. Agr. Food Chem. 2003, 51, 3144-3149;
[5] Chorfa et al., Appl. Catal. A: Gen. 2010, 387, 75-86.

REFERENCES CITED

Banni S, Day, B. W., Evans, R. W., Corongiu, F. P., Lombardi, B. (1994). J. Am. Oil Chem. Soc. 71:1324-1325
Bauer P, Horlacher, P., Claus, P. (2009). Chem. Eng. Technol. 32:2005-2010
Bernas A, Kumar, N., Laukkanen, P., Vayrynen, J., Salmi, T., Murzin, D. Y. (2004). Applied Catalysis a-General 267: 121-133
Bernas A, Kumar, N., Mäki-Arvela, P., Kul'kova, N. V., Holmbom, B., Salmi, T., Murzin, D. Y. (2003). Applied Catalysis a-General 245:257-275
Bhattacharya A, Banu J, Rahman M, Causey J, Fernandes G (2006). Journal of Nutritional Biochemistry 17:789-810
Chorfa N, Hamoudi, S., Belkacemi, K. (2010). Applied Catalysis a-General 387:75-86
Coakley M, Johnson, M. C., McGrath, E., Rahman, S., Ross, R. P., Fitzgerald, G. F., Devery, R., Stanton, C. (2006). Nutrition and Cancer 56:95-102
DeJarlais W J, Gast, L. E. (1971a). J. Am. Oil Chem. Soc. 48:157-159
DeJarlais W J, Gast, L. E. (1971b). J. Am. Oil Chem. Soc. 48:21-24
Deshpande V M, Gadkari, R. G., Mukesh, D., Narasimhan, C. S. (1985). J. Am. Oil Chem. Soc. 62:734-738
Ecker J, Liebisch, G., Patsch, W., Schmitz, G. (2009). Biochemical and Biophysical Research Communications 388: 660-666
Frankel E N (1970). J. Am. Oil Chem. Soc. 47:33-36
Jung M O, Ju, J. W., Choi, D. S., Yoon, S. H., Jung, M. Y. (2002). J. Am. Oil Chem. Soc. 79:501-510
Jung M O, Yoon, S. H., Jung, M. Y. (2001). J. Agric. Food Chem. 49:3010-3016 Kreich M, Claus, P. (2005). Angewandte Chemie 44:7800-7804
Larock R C, Dong, X., Chung, S., Reddy, C. K., Ehlers, L. E. (2001). J. Am. Oil Chem. Soc. 78:447-453
Lee Y, Vanden Heuvel, J. P. (2010). Journal of Nutritional Biochemistry 21:490-497 Mossoba M M, McDonald, R. E., Armstrong, D. J., Page, S. W. (1991). J. Chrom. Sci. 29:324-330
Mukesh D, Narasimhan, C. S., Deshpande, V. M., Ramnarayan, K. (1988). Ind. Eng. Chem. Res. 27:409-414
Mukesh D, Narasimhan, S., Gadkarl, R., Deshpande, V. M. (1985). Ind. Eng. Chem. Prod. Res. Dev. 24:318-323
Narasimhan S, Mukesh, D., Gadkarl, R., Deshpande, V. M. (1985). Ind. Eng. Chem. Prod. Res. Dev. 24:324-326
Pariza M W, Park, Y., Cook, M. E. (2001). Progress in Lipid Research 40:283-298
Pertici P, Ballantini, V., Catalano, S., Giuntoli, A., Malanga, C., Vitulli, G. (1999). J. Mol. Catal. A: Chem. 144:7-13
Saebo A, Skarie, C., Jerome, D., Haroldsson, G., (2002) U.S. Pat. No. 6,410,761.
Simakova O A, Lleino, A.-R., Campo, B., Maki-Arvela, P., Kordas, K., Mikkola, J.-P., Murzin, D. Y. (2010). Catal. Today 150:32-36
Singer H, Seibel, R., Mees, U. (1977). Fette Seifen Anstrichmittel 79:147-150
Singer H, Stein, W., Lepper, H. (1972). Fette Seifen Anstrichmittel 74:193-198

The invention claimed is:

1. A method for preparing conjugated polyunsaturated fatty acids by isomerisation of a nonconjugated PUFA comprising contacting a starting material containing a nonconjugated PUFA with a heterogeneous catalyst containing a finely dispersed catalytic metal supported on a mesoporous zeolite or zeolite-like material having microporous and mesoporous porosity, wherein said heterogenous catalyst has a low Brønsted acidity by the presence of large monovalent alkali metal cations associated with said support and wherein the dispersion of said metal as calculated by CO chemosorption is at least 30%.

2. The method according to claim 1 wherein the isomerisation reaction occurs in the absence of H$_2$ in the reaction medium or associated with the catalyst.

3. The method according to claim 1 wherein said finely dispersed metal is a noble metal or Ni.

4. The method according to claim 3 wherein said finely dispersed metal is Ru or Rh.

5. The method according to claim 1 wherein said mesoporous zeolite or zeolite like material having microporous and mesoporous porosity has a Si/Al ratio of at least 30.

6. The method according to claim 1 wherein said heterogeneous catalyst is a Ru/Cs, Ru/Rb, Ru/K, Ru/Na, Rh/Cs, Rh/Rb, Rh/K, or Ru/Na loaded zeolite of the MFI-, BEA-, MOR or FAU-type.

7. The method according to claim 1, wherein said PUFA in said starting material containing a nonconjugated PUFA is a free fatty acid or is esterified with an alcohol or glycerol.

8. The method according to claim 7 wherein said PUFA is linoleic acid or linolenic acid.

9. The method according to claim 1 wherein said starting material is an oil or fat.

10. The method according to claim 1 wherein the isomerisation reaction is carried out in solvent free conditions.

11. A method for the modification of the pore architecture of a zeolite comprising the step of (i) treating said zeolite with a NH$_4$OH-solution with a concentration ranging from 0.001 to 0.03 M to provide a modified zeolite.

12. The method according to claim 11 further comprising the step of (ii) introducing a catalytic metal in said zeolite.

13. The method according to claim 11 wherein said zeolite is first (partially) dealuminated by steaming or acid leaching.

14. The method according to claim 11 wherein said modified zeolite has a framework of the type FAU, MFI, BEA, FER or MOR.

15. The method according to claim 11 wherein said modified zeolite has a FAU-type framework and has a mesopore volume ranging between 0.10 and 0.3 mL/g, a micropore volume of at least 0.2 mL/g and a large micropore volume of at least 0.15 mL/g.

16. A method of catalyzing a reaction, the method comprising utilizing the modified zeolite produced according to claim 11 as a catalyst, the reaction selected from acylation, alkylation, dimerization, oligomerization, polymerization, hydrogenation, dehydrogenation, aromatization, isomerisation, hydrotreating, catalytic cracking or hydrocracking reaction.

17. A method of catalyzing a reaction, the method comprising utilizing the modified zeolite of claim 11 as a catalyst in a PUFA isomerisation reaction, wherein said modified zeolite comprise a finely dispersed noble metal or Ni.

* * * * *